(12) United States Patent
Dirisio et al.

(10) Patent No.: US 11,039,799 B2
(45) Date of Patent: Jun. 22, 2021

(54) BEARING SYSTEM FOR CONE BEAM COMPUTED TOMOGRAPHY

(71) Applicant: CARESTREAM HEALTH, INC., Rochester, NY (US)

(72) Inventors: Anthony Dirisio, Rochester, NY (US); Michael A. Litzenberger, Rochester, NY (US)

(73) Assignee: Carestream Health, Inc., Rochester, NY (US)

(*) Notice: Subject to any disclaimer, the term of this patent is extended or adjusted under 35 U.S.C. 154(b) by 100 days.

(21) Appl. No.: 16/487,116

(22) PCT Filed: Mar. 7, 2018

(86) PCT No.: PCT/US2018/021324
§ 371 (c)(1),
(2) Date: Aug. 20, 2019

(87) PCT Pub. No.: WO2018/165285
PCT Pub. Date: Sep. 13, 2018

(65) Prior Publication Data
US 2021/0128081 A1    May 6, 2021

Related U.S. Application Data

(60) Provisional application No. 62/469,083, filed on Mar. 9, 2017.

(51) Int. Cl.
*A61B 6/00* (2006.01)
*A61B 6/03* (2006.01)
*F16C 17/10* (2006.01)

(52) U.S. Cl.
CPC ............ *A61B 6/035* (2013.01); *A61B 6/4085* (2013.01); *A61B 6/4452* (2013.01); *F16C 17/10* (2013.01); *F16C 2316/10* (2013.01)

(58) Field of Classification Search
CPC ............................... A61B 6/035; F16C 17/10
See application file for complete search history.

(56) References Cited

U.S. PATENT DOCUMENTS

| | | | |
|---|---|---|---|
| 6,435,713 B1 | 8/2002 | Iizuka | |
| 2009/0216067 A1* | 8/2009 | Lebosse | A61B 6/4441 600/13 |
| 2011/0301449 A1* | 12/2011 | Maurer, Jr. | A61B 6/032 600/411 |

FOREIGN PATENT DOCUMENTS

WO    2016/014025    1/2016

OTHER PUBLICATIONS

Commonly Assigned U.S. Appl. No. 61/710,832, entitled: Extremity Scanner and Methods for Using the Same filed Oct. 8, 2012, by John Yorkston, et al.

(Continued)

*Primary Examiner* — Dani Fox

(57) ABSTRACT

A radiographic imaging apparatus includes elongated rigid guide rails having equivalent symmetrical shapes. Carriages attached to the guide rails are configured to move along a length of the guide rails and to support a portion of the imaging apparatus and to facilitate movement thereof along the guide rails. A first type spherical bearing assembly allows a gimbaled connection thereto while allowing substantially no axial movement. A second type spherical bearing assembly allows a gimbaled connection thereto while allowing a limited amount of axial movement. Frame mounts are each attached to one of the first type and second type spherical bearing assemblies to facilitate movement having a one sided tolerance along the guide rails.

12 Claims, 45 Drawing Sheets

(56) References Cited

OTHER PUBLICATIONS

International Search Report dated May 29, 2018 for International Application No. PCT/US2018/012324, 3 pages.
International Search Report dated May 29, 2018 for International Application No. PCT/US2018/021324, 3 pages.

* cited by examiner

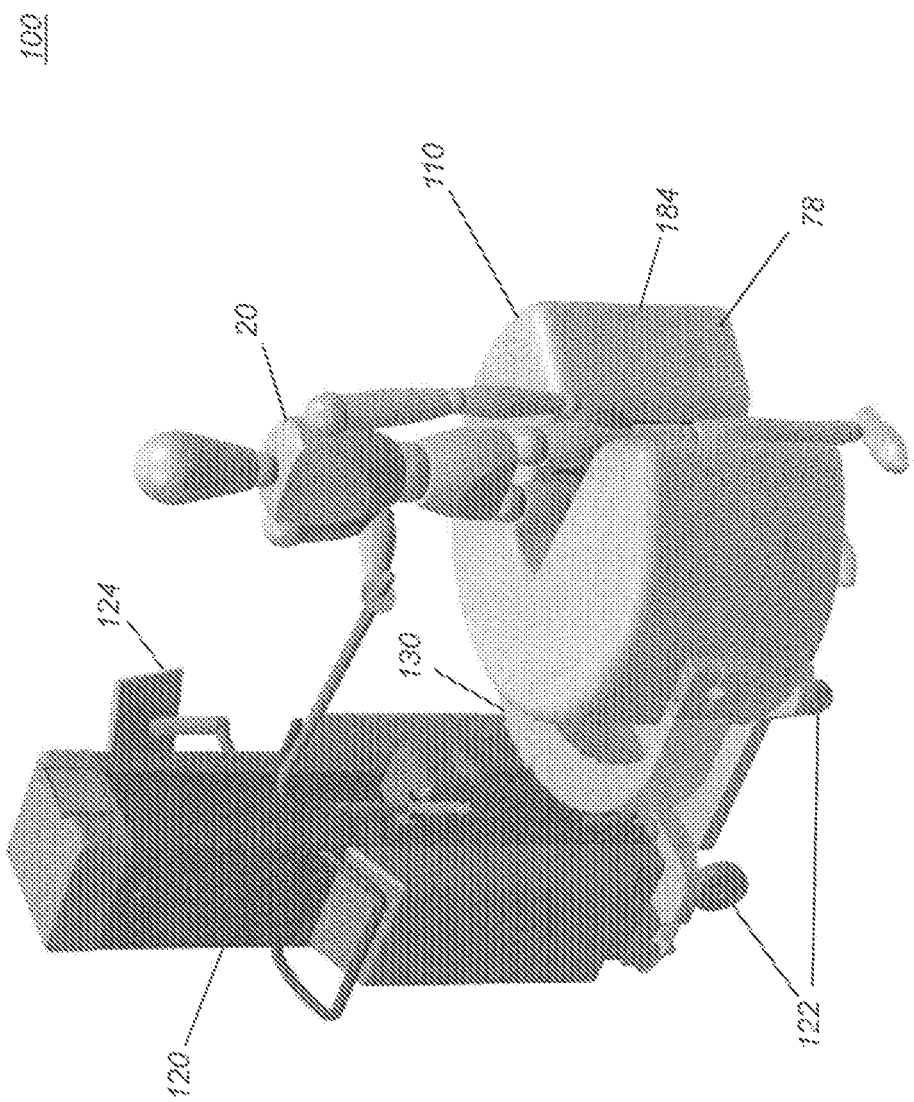

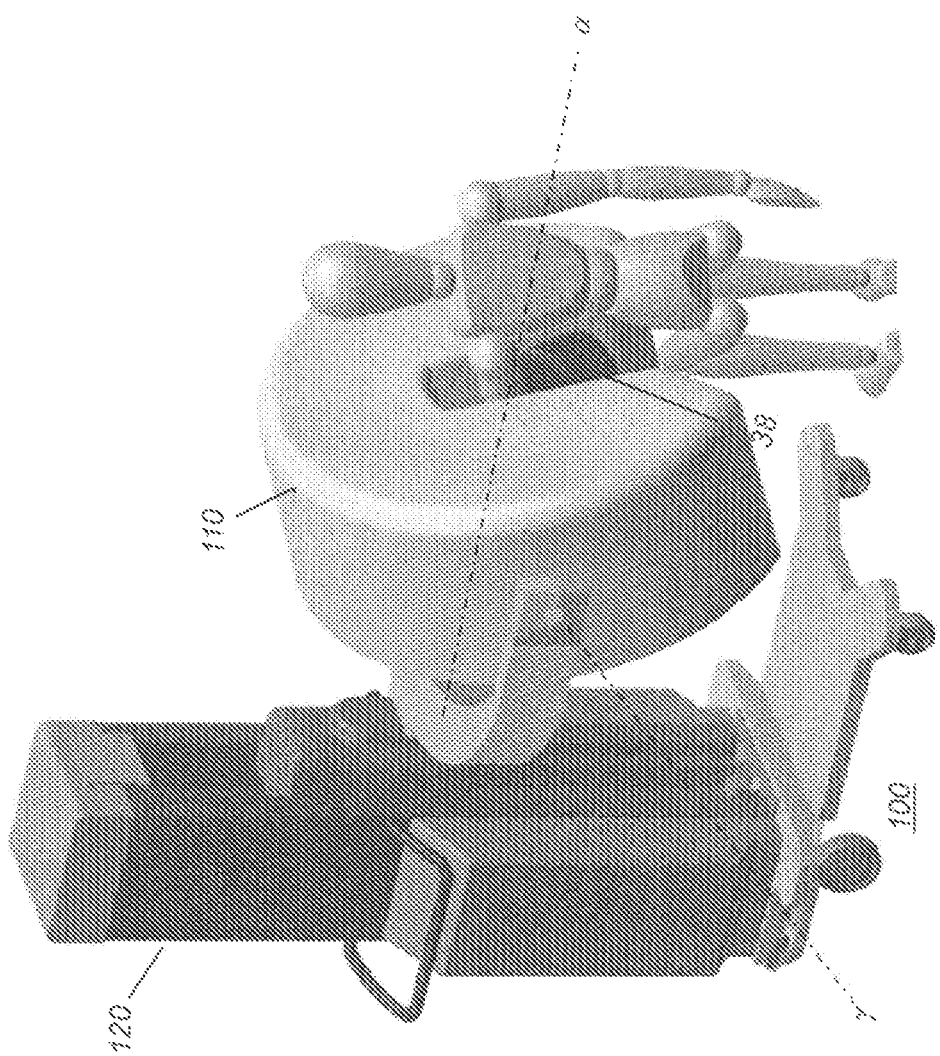

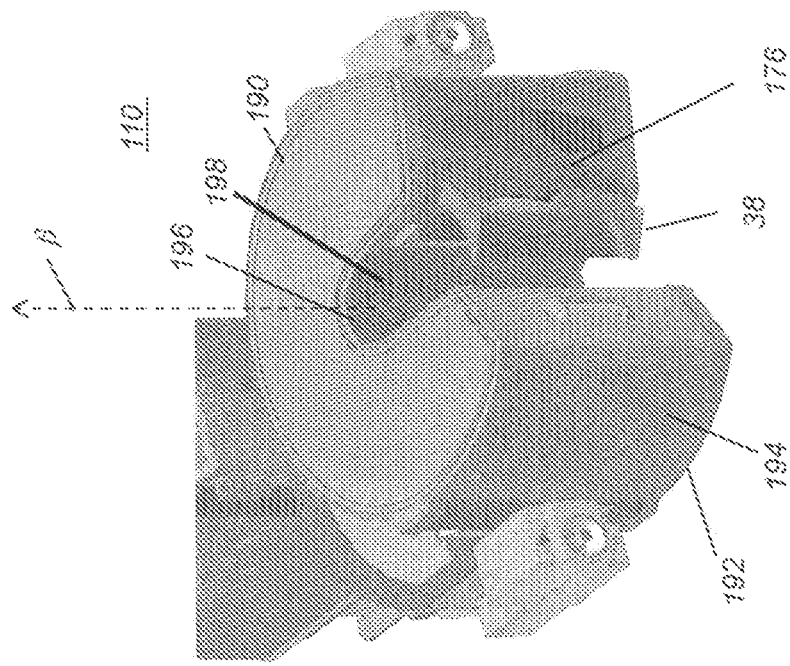
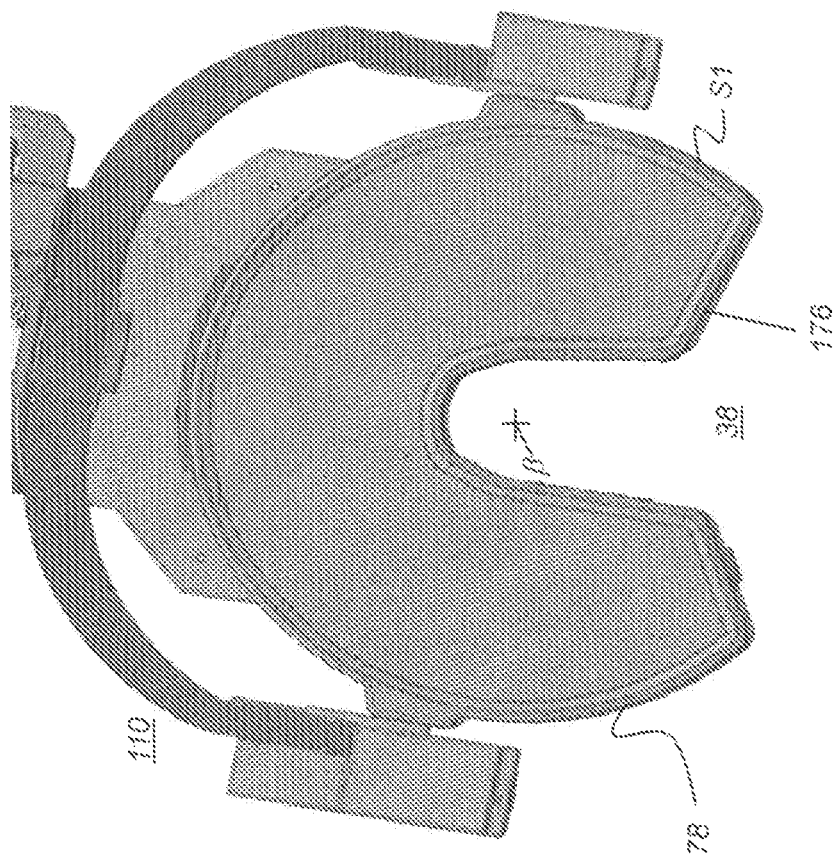
FIG. 13B
FIG. 13A

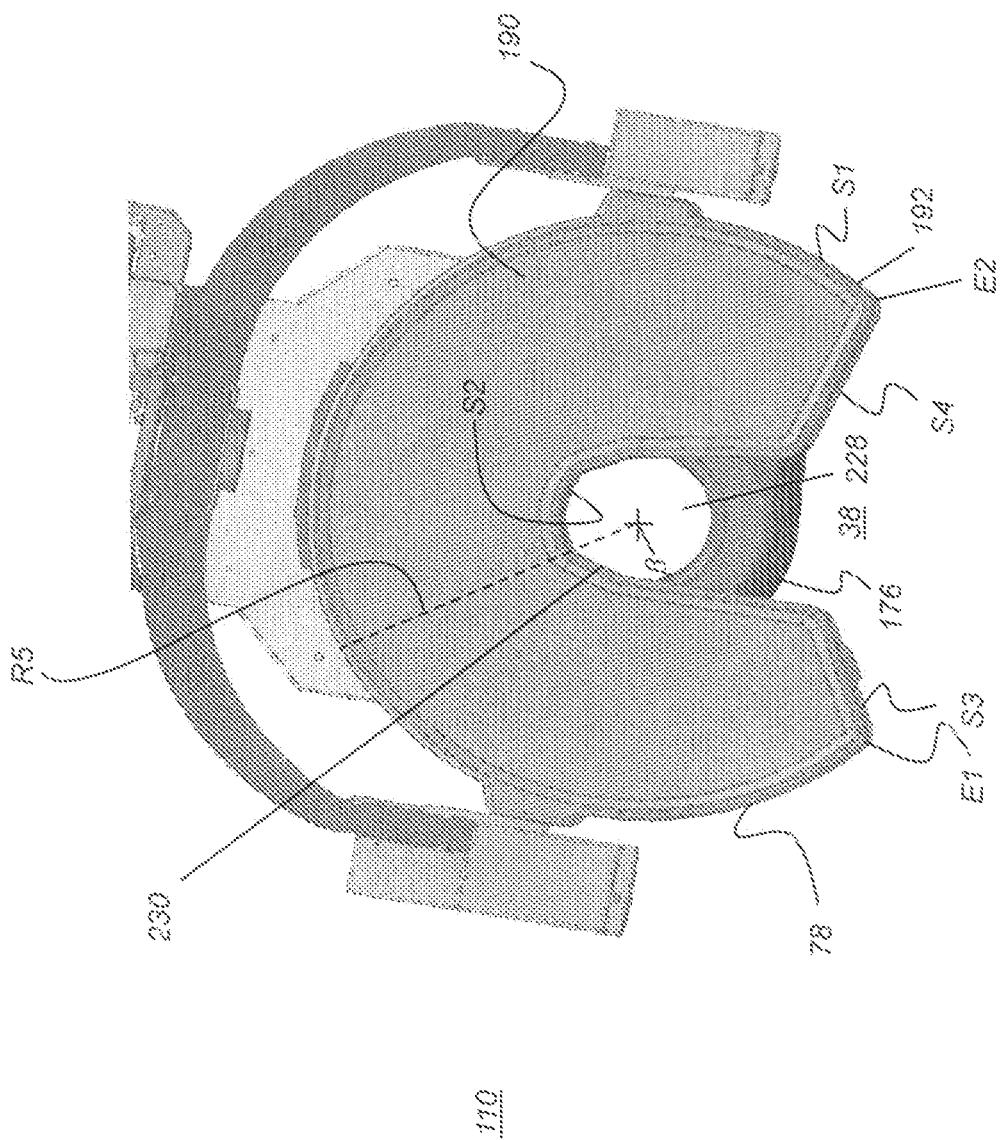

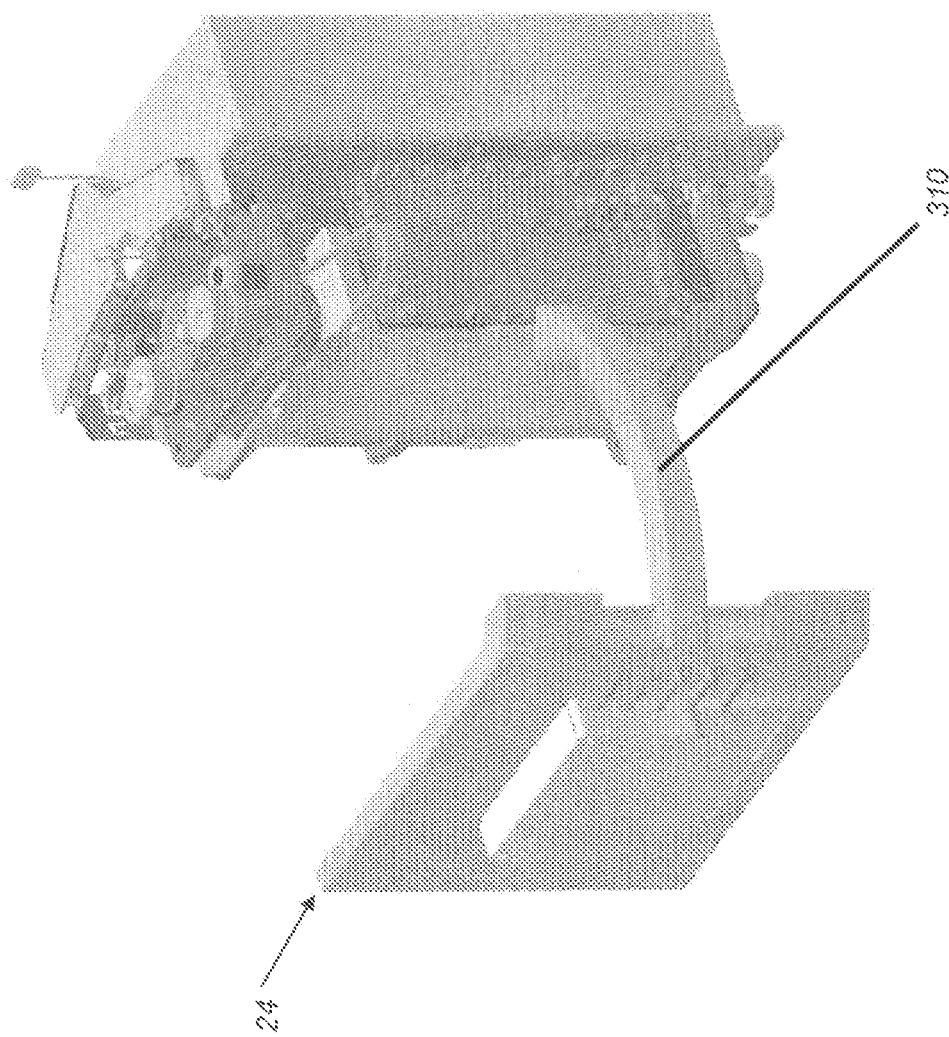

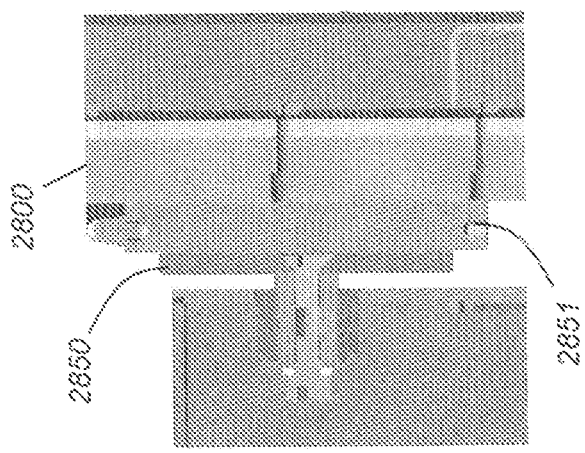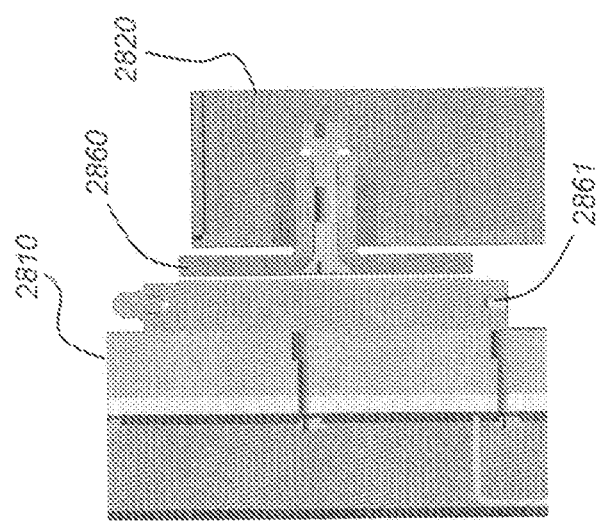
FIG. 28D

BEARING SYSTEM FOR CONE BEAM COMPUTED TOMOGRAPHY

CROSS REFERENCE TO RELATED APPLICATIONS

This application claims the benefit of and is a U.S. National Phase filing of PCT Application PCT/US2018/021324 filed Mar. 7, 2018 entitled "BEARING SYSTEM FOR CONE BEAM COMPUTED TOMOGRAPHY", in the name of Anthony Dirisio et al., which claims benefit of U.S. Patent Application Ser. No. 62/469,083, filed Mar. 9, 2017, in the name of Anthony Dirisio et al., and entitled BEARING SYSTEM FOR CONE BEAM COMPUTED TOMOGRAPHY.

FIELD OF THE INVENTION

The disclosure relates generally to diagnostic radiographic imaging systems and in particular to cone beam imaging systems used for obtaining volume images of patient extremities.

BACKGROUND

3-D volume imaging has proved to be a valuable diagnostic tool that offers significant advantages over earlier 2-D radiographic imaging techniques for evaluating the condition of internal structures and organs. 3-D imaging of a patient or other subject has been made possible by a number of advancements, including the development of high-speed imaging detectors, such as digital radiography (DR) detectors that enable multiple images to be taken in rapid succession.

Cone beam computed tomography (CBCT) technology offers considerable promise as one type of diagnostic tool for providing 3-D volume images. Cone beam CT systems capture volumetric data sets by using a high frame rate DR detector and an x-ray source, typically affixed to a gantry that rotates about the object to be imaged, directing, from various points along its orbit around the subject, a divergent cone beam of x-rays toward the subject. The CBCT system captures projections throughout the rotation, for example, one 2-D projection image at every degree of rotation. The projections are then reconstructed into a 3D volume image using various techniques. Among well known methods for reconstructing the 3-D volume image from the 2-D image data are filtered back projection approaches.

Although 3-D images of diagnostic quality can be generated using CBCT systems and technology, a number of technical challenges remain. In some cases, for example, there can be a limited range of angular rotation of the x-ray source and detector with respect to the subject. CBCT imaging of legs, arms, and other extremities can be hampered by physical obstruction from a paired extremity. This is an obstacle that is encountered in obtaining CBCT image projections for the human leg or knee, for example. Not all imaging positions around the knee are accessible; the patient's own anatomy often prevents the radiation source and image detector from being positioned over a portion of the scan circumference.

To illustrate the problem faced in CBCT imaging of the knee, the top view of FIG. 1 shows the circular scan paths for a radiation source 22 and detector 24 when imaging the right knee R of a patient as a subject 20. Various positions of radiation source 22 and detector 24 are shown in dashed line form. Source 22, placed at some distance from the knee, can be positioned at different points over an arc of about 200 degrees; with any larger arc the paired extremity, left knee L, blocks the way. Detector 24, smaller than source 22 and typically placed near subject 20, can be positioned between the patient's right and left knees and is thus capable of positioning over the full circular orbit.

A full 360 degree orbit of the source and detector is not needed for conventional CBCT imaging; instead, sufficient information for image reconstruction can be obtained with an orbital scan range that just exceeds 180 degrees by the angle of the cone beam itself, for example. However, in some cases it can be difficult to obtain much more than about 180 degree revolution for imaging the knee or other joints and other applications. Moreover, there can be diagnostic situations in which obtaining projection images over a certain range of angles has advantages, but patient anatomy blocks the source, detector, or both from imaging over that range.

Still other difficulties with conventional solutions for extremity imaging relate to poor image quality. For image quality, the CBCT sequence requires that the detector be positioned close to the subject and that the source of the cone beam radiation be at a sufficient distance from the subject. This provides the best image and reduces image truncation and consequent lost data.

CBCT imaging represents a number of challenges that also affect other types of volume imaging that employ a radiation source and detector orbiting an extremity over a range of angles. There are various tomographic imaging modes that can be used to obtain depth information for a scanned extremity.

In summary, the capability for stable movement and straightforward configuration and positioning of the imaging apparatus allows the advantages of CBCT imaging to be adaptable for use with a range of extremities, to obtain volume images under a suitable imaging modality, with the image extremity presented at a suitable orientation under both load-bearing and non-load-bearing conditions, and with the patient appropriately standing or seated.

In order to provide a compact CBCT imaging apparatus for extremity imaging, a versatile and compact system design is beneficial. Among challenges for this type of design is the need for controlled movement of the radiation source and detector in various orientations.

SUMMARY

A radiographic imaging apparatus includes elongated rigid guide rails having equivalent symmetrical shapes. Carriages attached to the guide rails are configured to move along a length of the guide rails and to support a portion of the imaging apparatus and to facilitate movement thereof along the guide rails. A first type spherical bearing assembly allows a gimbaled connection thereto while allowing substantially no axial movement. A second type spherical bearing assembly allows a gimbaled connection thereto while allowing a limited amount of axial movement. Frame mounts are each attached to one of the first type and second type spherical bearing assemblies to facilitate movement having a one sided tolerance along the guide rails.

In one embodiment, a radiographic imaging apparatus includes elongated rigid guide rails having parallel symmetrical shapes spaced apart substantially in parallel. Carriages are attached to the guide rails. A first type spherical bearing assembly is attached to one of the carriages and is configured to allow a gimbaled connection thereto while allowing substantially no axial movement. A second type spherical bearing assembly is attached to another one of the carriages and is configured to allow a gimbaled connection thereto while allowing a limited amount of axial movement perpendicular to the guide rail. Frame mounts are attached to the first type and second type spherical bearing assemblies to support a portion of the imaging apparatus and to facilitate movement thereof along the guide rails.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings are not necessarily to scale, emphasis generally being placed upon illustrating the features of certain embodiments of the invention. In the drawings, like numerals are used to indicate like parts throughout the various views. Thus, for further understanding of the invention, reference can be made to the following detailed description, read in connection with the drawings in which:

FIG. 5 is a perspective view that shows a CBCT imaging apparatus for extremity imaging according to an embodiment of the application.

FIG. 11 is a perspective view that shows the extremity imaging apparatus configured for elbow imaging with a seated patient.

FIG. 13A is a top view of the imaging scanner showing the door open position.

FIG. 13B is a perspective view of the imaging scanner showing a door closing position.

FIG. 14C is a top view of the imaging scanner with its housing shown.

FIGS. 18A-18D are diagrams that show an exemplary embodiment of a counterweight support mechanism for use with a gantry for a transport mechanism for use in CBCT X-ray imaging systems according to the application.

FIG. 28D is a perspective view that shows carriage connections.

DESCRIPTION OF EXEMPLARY EMBODIMENTS

Figure 2:
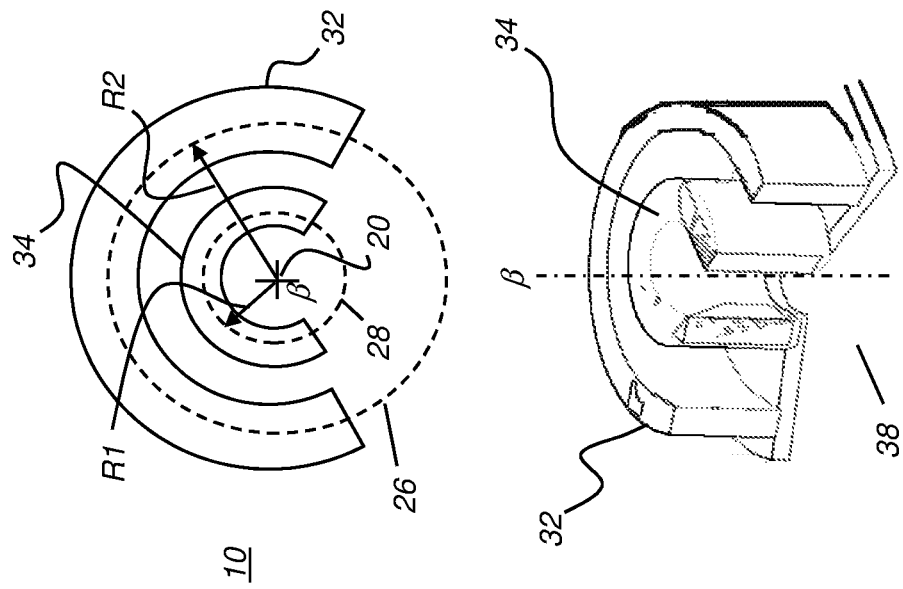
FIG. 2 shows a top and perspective view of the scanning pattern for an imaging apparatus according to an embodiment of the application.
Figure 1:
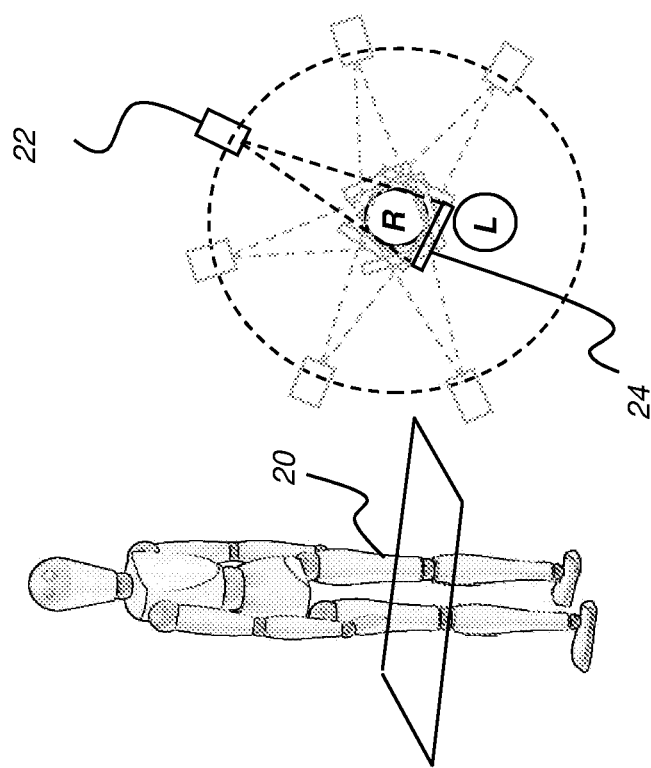
FIG. 1 is a schematic view showing the geometry and limitations of CBCT scanning for portions of the lower leg.

This application claims the benefit of U.S. Provisional application U.S. Ser. No. 62/469,083 filed Mar. 9, 2017, entitled "Bearing System for Cone Beam Computed Tomography" in the names of Anthony Dirisio and Michael A. Litzenberger, which is hereby incorporated by reference herein in its entirety.

In the context of the application, the term "extremity" has its meaning as conventionally understood in diagnostic imaging parlance, referring to knees, legs, ankles, fingers, hands, wrists, elbows, arms, and shoulders and any other anatomical extremity. The term "subject" is used to describe the extremity of the patient that is imaged, such as the "subject leg", for example. The term "paired extremity" is used in general to refer to any anatomical extremity wherein normally two or more are present on the same patient. In the context of the application, the paired extremity is not imaged unless necessary; only the subject extremity is imaged.

A number of the examples given herein for extemporary embodiments of the application focus on imaging of the load-bearing lower extremities of the human anatomy, such as the leg, the knee, the ankle, and the foot, for example. However, these examples are considered to be illustrative and non-limiting.

In the context of the application, two elements are considered to be substantially orthogonal if their angular orientations differ from each other by 90 degrees, +/−no more than about 10 degrees.

Certain exemplary embodiments disclosed herein address the difficulties of extremity imaging by providing an imaging apparatus that defines coordinated non-linear source and detector paths (e.g., orbital, curved, or concentric about a center point), wherein components that provide the source and detector paths are configured to allow patient access prior to and following imaging and configured to allow the patient to sit or stand with normal posture during the CBCT image capture series. Certain exemplary embodiments provide this capability by using a detector transport device that has a circumferential access opening allowing positioning of the extremity, wherein the detector transport device is revolved about the positioned extremity once it is in place, enclosing (e.g., partially, substantially, fully) the extremity as it is revolved through at least a portion of the scan.

It is instructive to consider dimensional attributes of the human frame that can be considerations for design of CBCT equipment for scanning extremities. For example, an adult human patient of average height in a comfortable standing position has left and right knees generally anywhere from about 10 to about 35 cm apart. For an adult of average height, exceeding about 35-40 cm (14-15.7 inches) between the knees becomes increasing less comfortable and out of the range of normal standing posture. It is instructive to note that this constraint makes it impractical to use conventional gantry solutions for obtaining the needed 2-D image sequence. For certain exemplary embodiments, either the source or the detector must be able to pass between the legs of a standing patient for knee CBCT imaging, a capability not available with gantry or other conventional solutions.

The perspective and corresponding top views of FIG. 2 show how the scanning pattern is provided for components of CBCT imaging apparatus 10 according to an embodiment of the application. A detector path 28 of a suitable radius R1 from a central axis β is provided for a detector device by a detector transport 34. A source path 26 of a second, larger radius R2 is provided for a radiation source by a source transport 32. In one embodiment, a non-linear source path 26 is greater in length than a non-linear detector path 28. According to an embodiment of the application, described in more detail subsequently, the same transport system provides both detector transport 34 and source transport 32. The extremity, subject 20, is preferably substantially centered along central axis β so that central axis β can be considered as a line through points in subject 20. In one embodiment, an imaging bore or the CBCT apparatus can include or encompass the central axis β. The limiting geometry for image capture is due to the path of source transport 32 blocked by patient anatomy, such as by a paired limb in the gap 38, and thus limited typically to less than about 220 degrees, as noted previously. The circumferential gap or opening 38 can occupy the space between the endpoints of the arc of source path 26. Gap or opening 38 gives space for the patient a place to stand, for example, while one leg is being imaged.

Figure 3C:
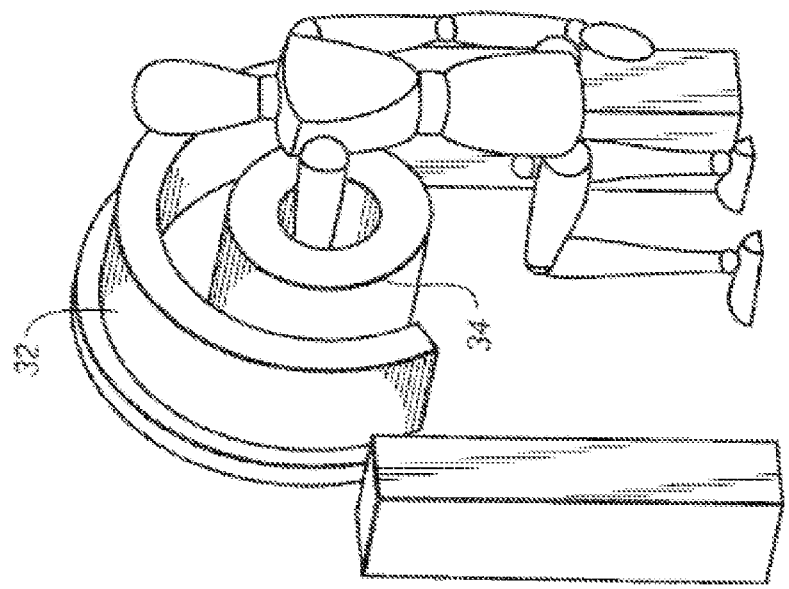
FIG. 3C is a perspective view showing patient access to another imaging apparatus according to an embodiment of the application.
Figure 3A:
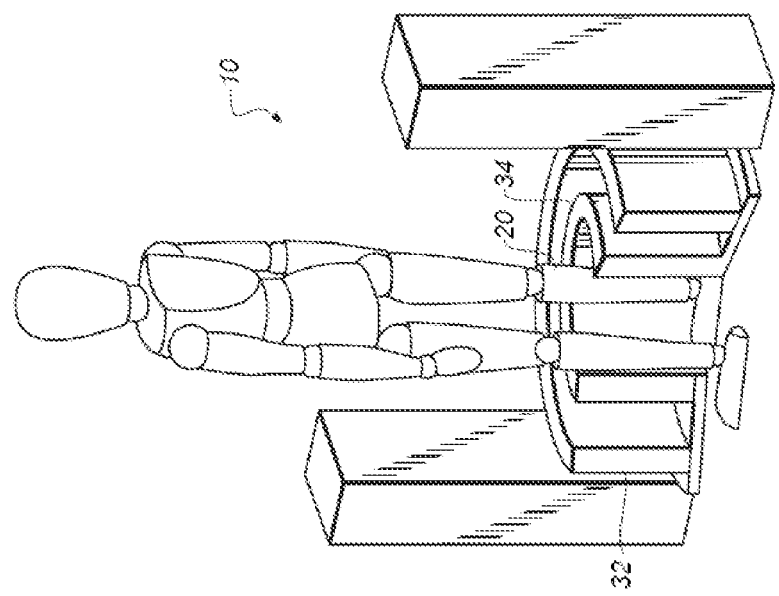
FIG. 3A is a perspective view showing patient access to an imaging apparatus according to an embodiment of the application.
Figure 3B:
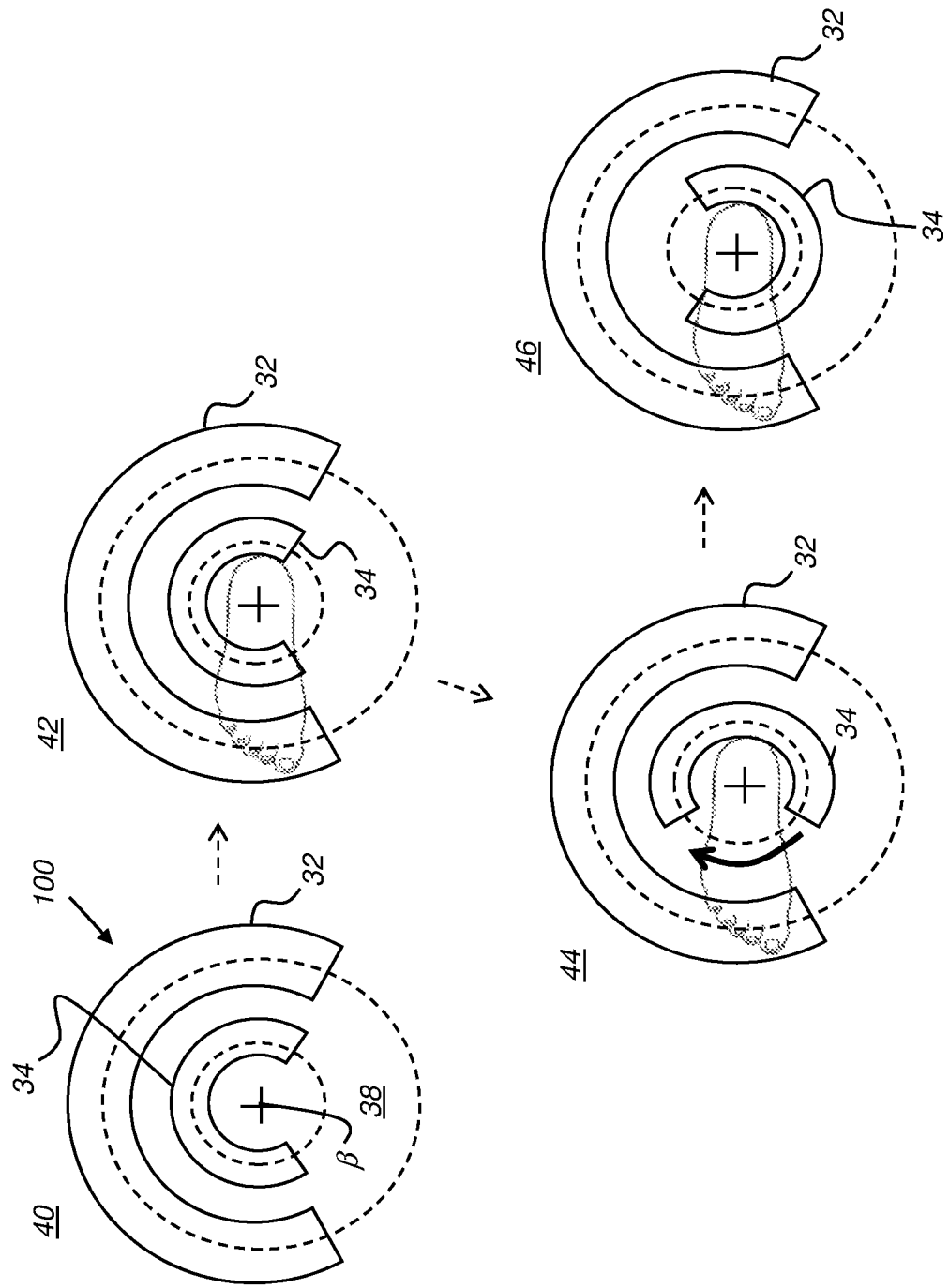
FIG. 3B is a top view showing a sequence of steps for enclosing the extremity to be imaged within the path of the detector transport.
Figure 3D:
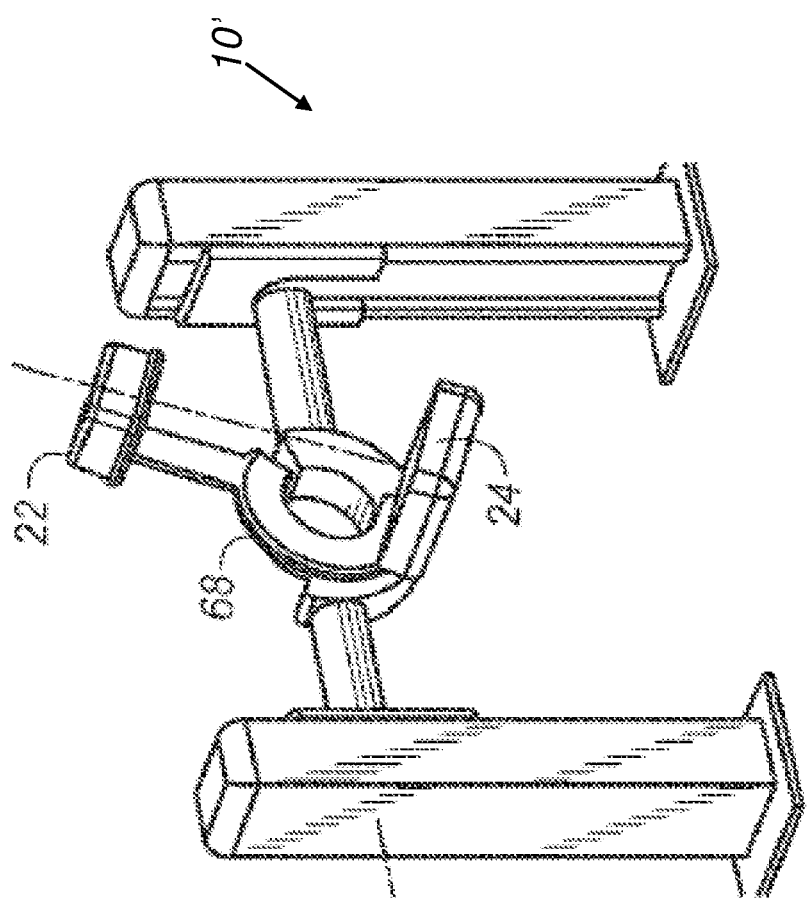
FIG. 3D is a perspective view showing a revolvable gantry for another imaging apparatus according to an embodiment of the application.

Detector path 28 can extend through circumferential gap 38 to allow scanning, since the detector is not necessarily blocked by patient anatomy but can have a travel path at least partially around an imaged extremity that can extend between the standing patient's legs. Embodiments of the present invention allow temporary restriction of the detector path 28 to allow access for the patient as part of initial patient positioning. The perspective view in FIG. 2, for example, shows detector transport 34 rotated to open up circumferential gap 38 so that it extends from the axis β (e.g., beyond a source path or housing). With detector transport 34 translated to the open position shown in FIG. 3A, the patient can freely move in and out of position for imaging. When the patient is properly in position, detector transport 34 is revolved about axis β by more than 180 degrees; according to an embodiment of the application, detector transport 34 is revolved about axis β by substantially 200 degrees. This patient access and subsequent adjustment of detector transport 34 is shown in successive stages 40, 42, 44, 46 in FIG. 3B. This orbital movement confines the extremity to be imaged more effectively and places detector 24, not visible in FIGS. 2-3C due to the detector transport 34 housing, in position near subject 20 for obtaining the first projection image in sequence. In one embodiment, detector transport 34 can include shielding or a door over part of the detector path, and/or the gap 38. As shown in FIG. 3D, a revolvable gantry 68 allows detector 24 and source 22 to revolve around imaging volume of another imaging apparatus 10' according to an embodiment of the application.

Circumferential gap or opening 38 not only allows access for positioning of the subject leg or other extremity, but also allows sufficient space for the patient to stand in normal posture during imaging, placing the subject leg for imaging in the central position along axis β (FIG. 2) and the non-imaged paired leg within the space defined by circumferential gap 38. Circumferential gap or opening 38 extends approximately 180 degrees minus the fan angle (e.g., between ends of the source path), which is determined by source-detector geometry and distance. Circumferential gap or opening 38 permits access of the extremity so that it can be centered in position along central axis β. Once the patient's leg or other extremity is in place, detector transport 34, or a hooded cover or hollow door or other member that defines this transport path, can be revolved into position, closing the detector portion of circumferential gap or opening 38.

Figure 4:
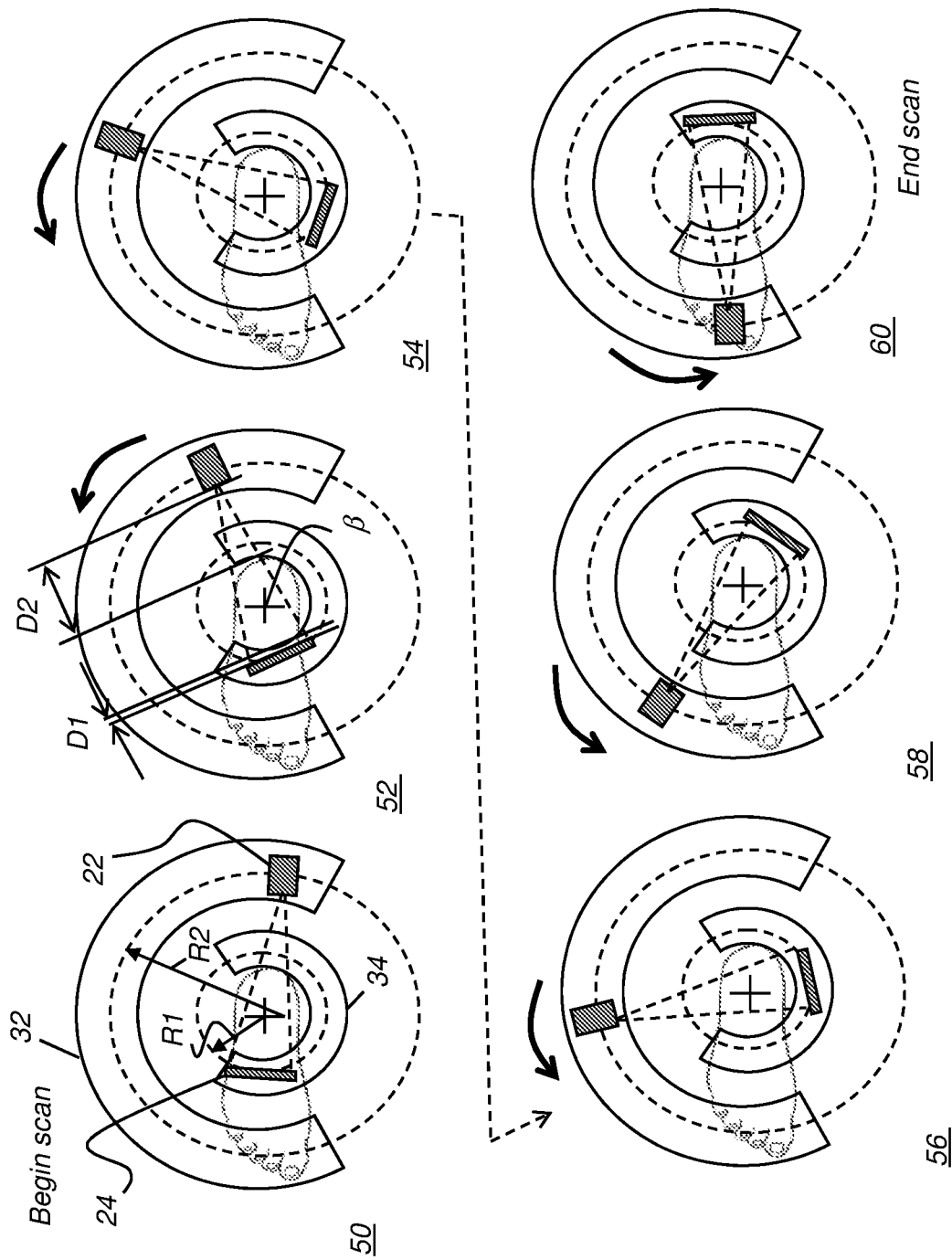
FIG. 4 shows portions of the operational sequence for obtaining CBCT projections of a portion of a patient's leg at a number of angular positions when using the imaging apparatus according to an embodiment of the application.

By way of example, the top views of FIG. 4 show portions of the operational sequence for obtaining CBCT projections of a portion of a patient's leg at a number of angular positions when using a CBCT imaging apparatus. The relative positions of radiation source 22 and detector 24, which may be concealed under a hood or chassis, as noted earlier, are shown in FIG. 4. The source 22 and detector 24 can be aligned so the radiation source 22 can direct radiation toward the detector 24 (e.g., diametrically opposite) at each position during the CBCT scan and projection imaging. The sequence begins at a begin scan position 50, with radiation source 22 and detector 24 at initial positions to obtain an image at a first angle. Then, both radiation source 22 and detector 24 revolve about axis β (e.g., imaging volume) as represented in interim scan positions 52, 54, 56, and 58. Imaging terminates at an end scan position 60. As this sequence shows, source 22 and detector 24 are in opposing positions relative to subject 20 at each imaging angle. Throughout the scanning cycle, detector 24 is within a short distance D1 of subject 20. Source 22 is positioned beyond a longer distance D2 of subject 20. The positioning of source 22 and detector 24 components on each path can be carried out by separate actuators, one for each transport path, or by a single rotatable member, as described in more detail subsequently. It should be noted that scanning motion in the opposite direction, that is, clockwise with respect to the example shown in FIG. 4, is also possible, with the corresponding changes in initial and terminal scan positions.

Figure 6B:
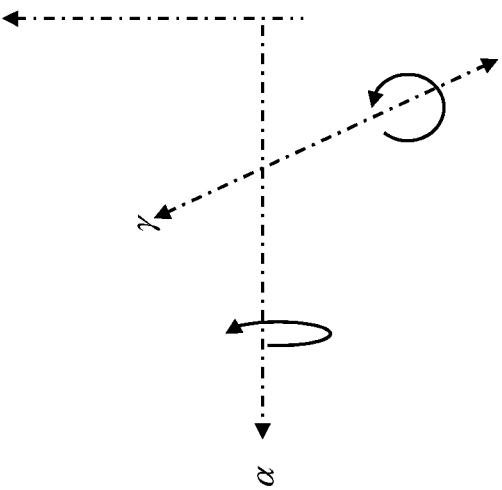
FIG. 6B shows reference axes for rotation and translation.
Figure 6A:
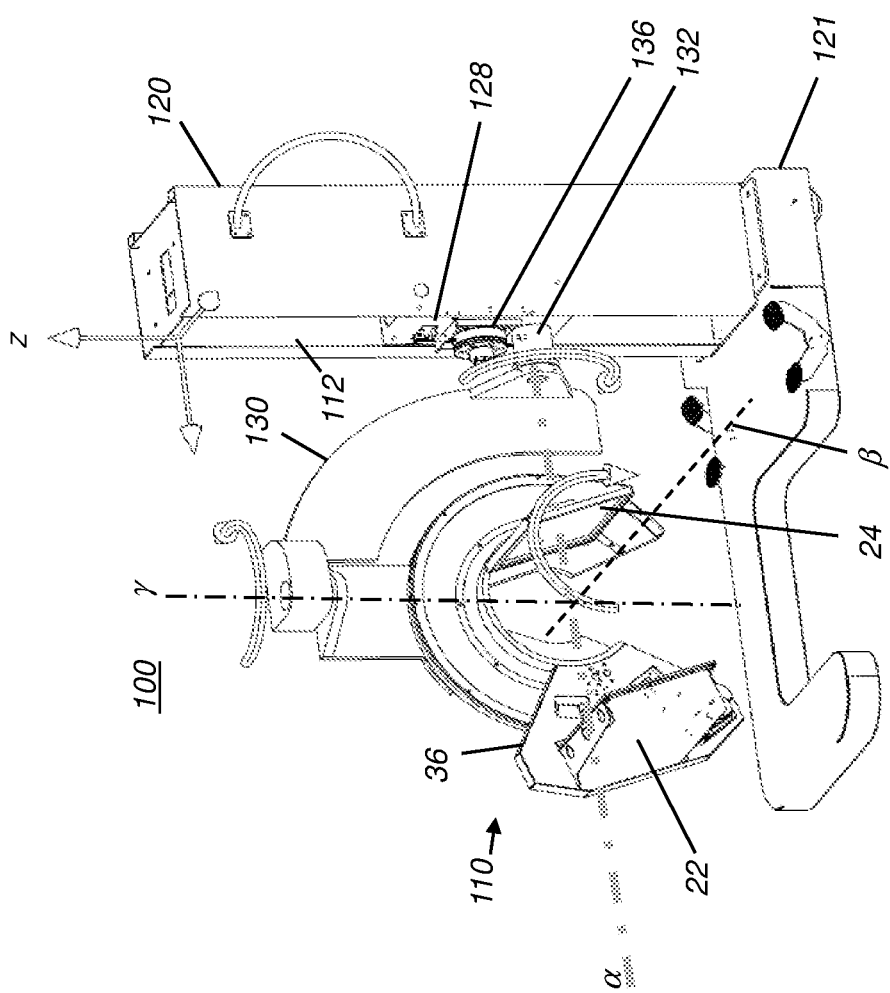
FIG. 6A shows internal components used for imaging ring translation and positioning.

Given this basic operation sequence in which the source 22 and detector 24 orbit the extremity, the usefulness of an imaging system that is adaptable for imaging patient extremities with the patient sitting or standing and in load-bearing or non load-bearing postures can be appreciated. The perspective view of FIG. 5 shows a CBCT imaging apparatus 100 for extremity imaging according to an embodiment of the application. Imaging apparatus 100 has a gimballed imaging ring or scanner 110 that houses and conceals source 22 and detector 24 within a housing 78 that provides a cover 184. FIG. 5 shows their supporting transport mechanisms. Scanner 110 is adjustable in height and rotatable in gimbaled fashion about non-parallel axes, such as about substantially orthogonal axes as described in subsequent figures, to adapt to various patient postures and extremity imaging conditions. A support column 120 supports scanner 110 on a yoke, or bifurcated or forked support arm 130, a rigid supporting element that has adjustable height and further provides rotation of scanner 110 as described subsequently. Support column 120 can be fixed in position, such as mounted to a floor, wall, or ceiling. According to portable CBCT embodiments such as shown in FIG. 6A and elsewhere, support column 120 mounts to a support base 121 that also includes optional wheels or casters 122 for transporting and maneuvering imaging apparatus 100 into position. A control panel 124 can provide an operator interface, such as a display monitor, for entering instructions for apparatus 100 adjustment and operation. In one embodiment, the control panel 124 can include a processor or computer (e.g., hardware, firmware and/or software) to control operations of the CBCT system 100. Support column 120 can be of fixed height or may have telescoping operation, such as for improved visibility when apparatus 100 is moved.

FIG. 6A shows portions of exemplary internal imaging and positioning mechanisms (with covers removed) for scanner 110 that allow imaging apparatus 100 the capability for imaging extremities with a variety of configurations. FIG. 6B shows rotation axes definitions for scanner 110 positioning. The α-axis and the γ-axis are non-parallel, to allow gimbaled action. According to an embodiment of the application as shown in FIG. 6A, the α-axis and the γ-axis are mutually orthogonal. The α-axis is substantially orthogonal to the z-axis. The intersection of the α-axis and the γ-axis can be offset from support column 120 by some non-zero distance.

First considering the z-axis, FIG. 6A shows an exemplary embodiment to achieve vertical motion. Within support column 120, a vertical carriage translation element 128 is actuated in order to travel upwards or downwards along column 120 within a track 112 along a transport path extending in a vertical (z-axis) direction. Carriage translation element 128 has a support shaft 132 that is coupled to an actuator 136 for providing α-axis rotation to forked or C-shaped support arm 130. Forked support arm 130, shown only partially in FIG. 6A to allow a better view of underlying components, is coupled to support shaft 132. X-ray source 22 and receiver 24 are mounted on a rotatable gantry 36 for rotation about a scan or central axis, designated as the β axis. Axis β is orthogonal to the α-axis and the γ-axis.

It can be appreciated that z-axis translation can be effected in a number of ways. Challenges that must be addressed by the type of system that is used include handling the weight of forked support arm 130 and the imaging scanner 110 that arm 130 supports. This can easily weigh a few hundred pounds. In addition, precautions must be provided for handling conditions such as power loss, contact with the patient, or mechanical problems that hamper positioning movement or operation. Forked support arm 130 can support scanner 110 in a gimbaled arrangement. Source 22 and detector 24 are shown on gantry 36 for reference in FIG. 6A. Vertical carriage translation element 128 is configured to ride within a track 112 within support column 120. For certain exemplary embodiments, some level of manual operability can be provided, such as for power loss situations.

According to an alternate embodiment of the application, vertical carriage translation element 128 can be a motor that moves vertically along supporting threaded shaft 132; alternately, vertical carriage translation element 128 can be driven using a chain, pulley, or other intermediate mechanism that has considerable counterweights for manually raising and lowering vertical carriage translation element 128 and its connected forked support arm 130 and components within support column 120.

Next, considering the α-axis movement of forked support arm 130, in one embodiment a rotational actuator 136 can be energizable to allow rotation of shaft 132 (FIG. 6A). This rotational actuation can be concurrent with z-axis translation as well as with rotation with respect to the γ-axis. X- and y-axes are indicated for reference.

Forked support arm 130 allows movement relative to the γ-axis according to the position and angle of forked support arm 130. In the example of FIG. 6A, the γ-axis is oriented vertically, substantially in parallel with the z-axis.

Figure 7B:
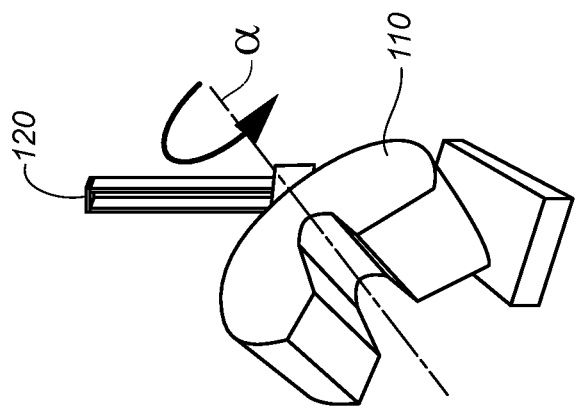
FIG. 7B shows rotation of the imaging ring about an α-axis that is orthogonal to the z-axis.
Figure 7A:
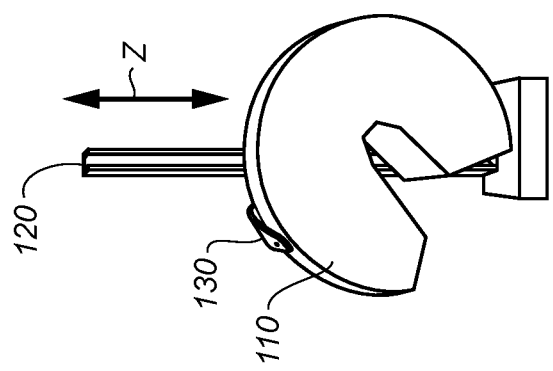
FIG. 7A shows translation of the imaging ring with respect to a vertical or z-axis.
Figure 7C:
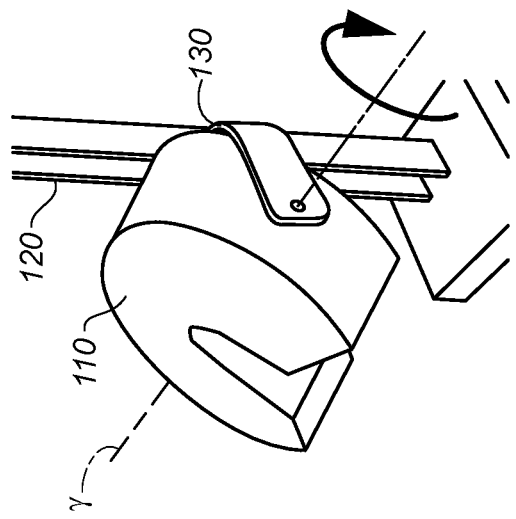
FIG. 7C shows rotation of the imaging ring about a γ-axis that is orthogonal to the α-axis.

An exemplary positioning capability of the imaging apparatus 100 is shown in FIGS. 7A-7C. FIG. 7A shows movement of forked support arm 130 on support column 120 to provide z-axis (vertical) translation of scanner 110. FIG. 7B shows rotation of forked support arm 130 about the horizontal α-axis. FIG. 7C shows rotation about the γ-axis as defined by the C-arm arrangement of forked support arm 130.

According to an exemplary embodiment, an initial set of operator commands automatically configure CBCT imaging apparatus 100 to one of a well-defined set of default positions for imaging, such as those described subsequently. The patient waits until this initial setup is completed. Then, the patient is positioned at CBCT imaging apparatus 100 and any needed adjustments in height (z-axis) or rotation about the α or γ axes can be made by the technician. This type of fine-tuning adjustment is at slow speeds for increased patient comfort and because only incremental changes to position are needed in most cases.

In addition to the z-axis translation and rotation about α- and γ-axes previously described, casters 122 allow rotation of scanner 110 position with respect to the z-axis as well as translation along the floor.

Given the basic structure described with reference to FIGS. 6A-7C, the positioning versatility of scanner 110 for various purposes can be appreciated. Subsequent FIGS. 8-11 show, by way of example, how this arrangement serves different configurations for extremity imaging.

Figure 8:
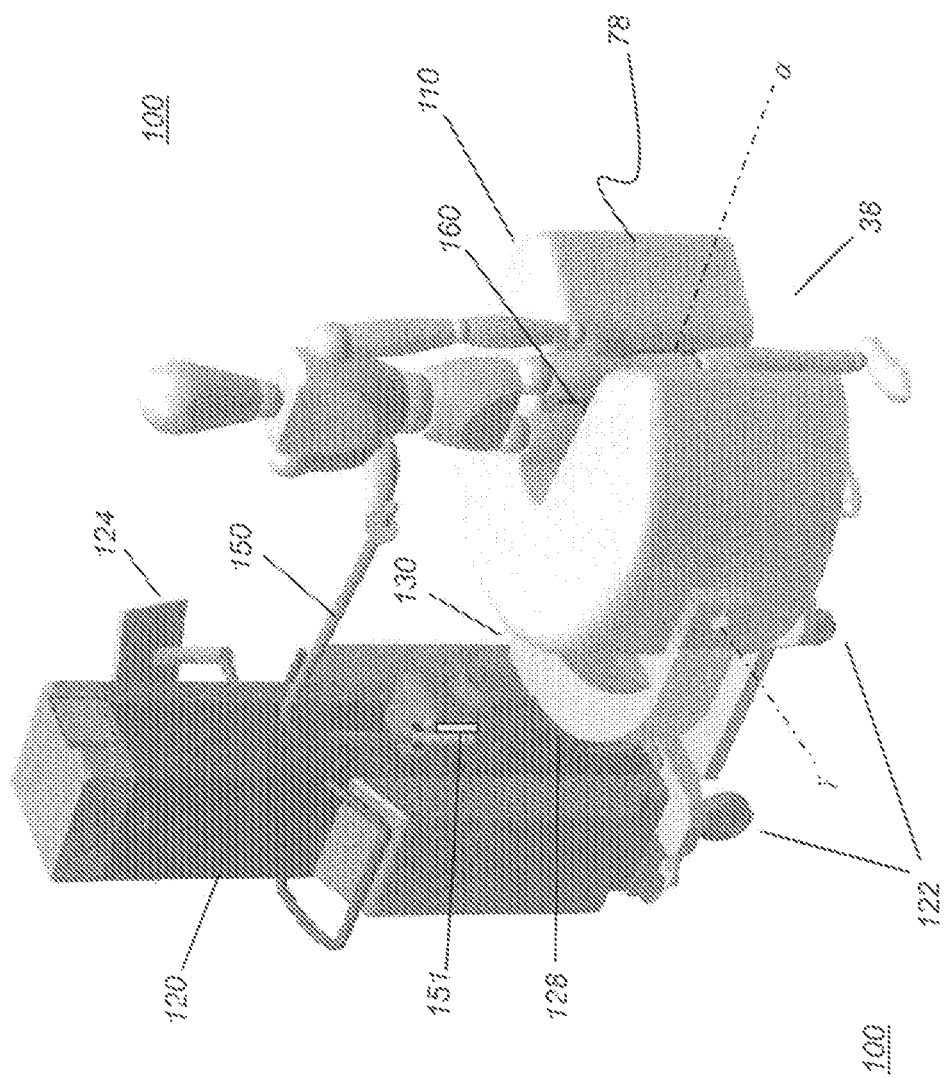
FIG. 8 is a perspective view that shows the extremity imaging apparatus configured for knee imaging with a standing patient.

FIG. 8 shows an exemplary scanner 110 positioning for a knee exam, where subject 20 is a standing patient. An optional patient support arm or bar 150 can be attached to support column 120. In one embodiment, support bar 150 is mounted to vertical carriage translation element 128. Accordingly, as the vertical carriage translation element 128 moves, a corresponding position of the support bar 150 can be moved. According to an alternate embodiment of the application, the support bar 150 can be mounted to the scanner 110, such as to the cover of scanner 110 or to the forked support arm 130. In contrast, embodiments of support bar 150 can be motionless during imaging or during a scan by the scanner 110. For this embodiment, vertical adjustment along the z-axis sets the knee of the patient at the center of the scanner 110. Forked support arm 130 is arranged so that the plane that contains both the α-axis and the γ-axis is substantially horizontal. Patient access is through an opening, circumferential gap or opening 38 in scanner 110. A door 160 is pivoted into place across gap 38 to enclose an inner portion of circumferential gap or opening 38. Door 160 fits between the legs of the patient once the knee of the patient is positioned.

Figure 9:
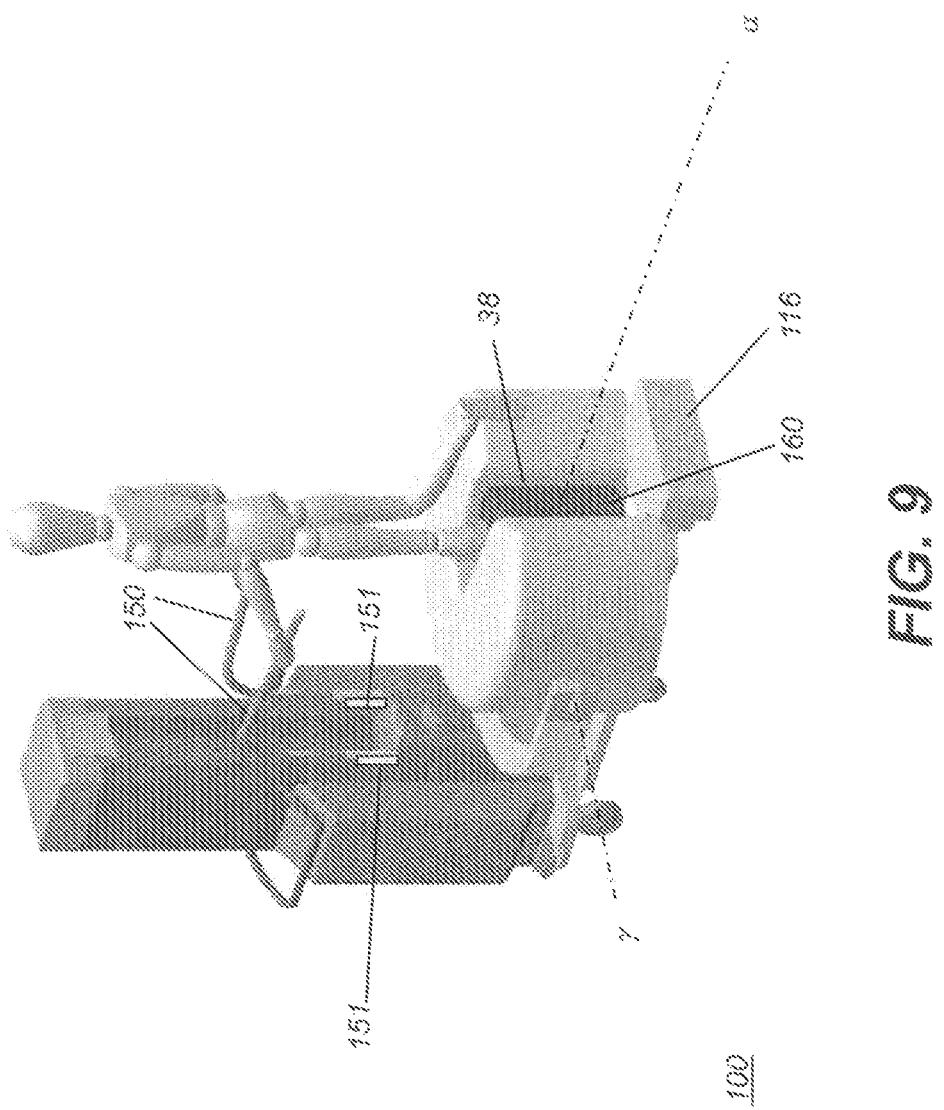
FIG. 9 is a perspective view that shows the extremity imaging apparatus configured for foot or ankle imaging with a standing patient.

Certain exemplary embodiments of optional patient support bar 150 can be mounted to movable portions of the CBCT apparatus 100, preferably to have a prescribed spatial relationship to an imaging volume. For such embodiments, a presence detector 151 can be configured to detect when the support bar 150 is mounted to the CBCT system 100. When detected, a controller or the like, for example, in the control panel 124, can calculate scanner 110, and/or forked support arm 130 movements to prevent collisions therebetween with the affixed support bar 150. Thus when attached, support bar 150 can limit motion of the scanner 110. Exemplary presence detectors 151 can include but are not limited to magnetic detectors, optical detectors, electro-mechanical detectors or the like. As shown in FIG. 9, a pair of optional or removable support arms 150 can be affixed to the vertical carriage translation element 128 and have their attachment reported by a pair of presence detectors 151.

For FIG. 8 and selected subsequent exemplary embodiments, door 160, once pivoted into its closed position, can effectively extend the imaging path by protecting and/or providing the curved detector transport 34 path as shown in FIG. 4. With this arrangement, when door 160 is closed to protect the transport path, the knee can be examined under weight-bearing or non-weight-bearing conditions. By enclosing the portion of detector transport 34 path that crosses opening 38, door 160 enables the extremity to be positioned suitably for 3D imaging and to be maintained in position between the source and detector as these imaging components orbit the extremity in the CBCT image capture sequence.

FIG. 9 shows scanner 110 positioning for a foot or ankle exam wherein subject 20 is a standing patient. With this configuration, scanner 110 is lowered to more effectively scan the area of interest. The plane that contains both the α-axis and the γ-axis is approximately 10 degrees offset from horizontal, rotated about the γ axis. A step 116 is provided across circumferential gap or opening 38 for patient access.

Figure 10:
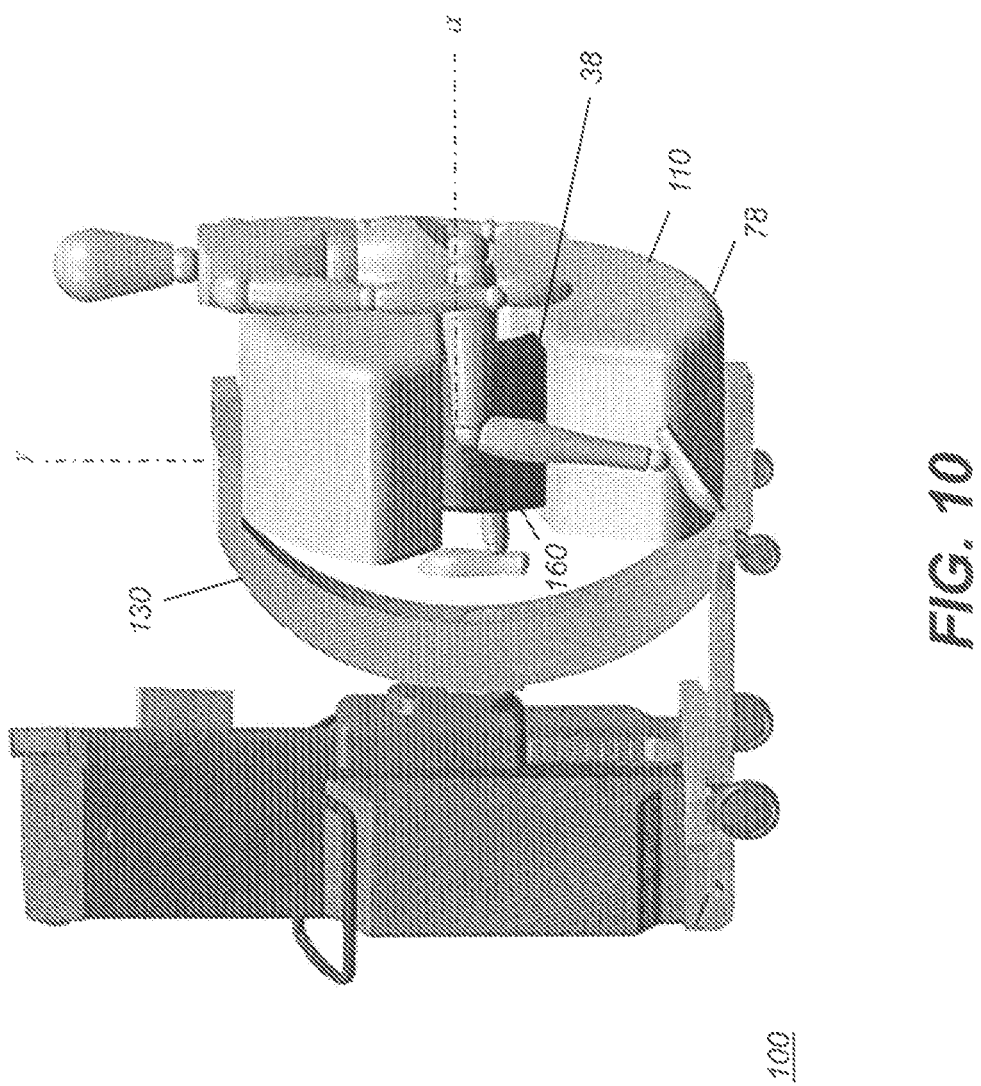
FIG. 10 is a perspective view that shows the extremity imaging apparatus configured for knee imaging with a seated patient.

FIG. 10 shows scanner 110 positioning for a knee exam with the patient seated. For this configuration, forked support arm 130 is elevated with respect to the z-axis. Rotation about the α-axis orients the γ-axis so that it is vertical or nearly vertical. Circumferential gap or opening 38 is positioned to allow easy patient access for imaging the right knee. It should be noted that 180 degree rotation about the γ-axis would position circumferential gap or opening 38 on the other side of scanner 110 and allow imaging of the other (left) knee.

Alternative scanner 110 positioning can include foot or ankle exam with the patient seated, toe exam with the patient seated, a hand exam, with the patient seated.

FIG. 11 shows scanner 110 positioning for an elbow exam, with the patient seated. For this configuration, forked support arm 130 is again elevated with respect to the z-axis. Rotation about the γ-axis positions circumferential gap 38 suitably for patient access. Further rotation about the α-axis may be provided for patient comfort.

In one embodiment of CBCT imaging apparatus 100, the operator can first enter an instruction at the control console or control panel 124 that specifies the exam type (e.g., for the configurations shown in FIGS. 8-11). The system then automatically adapts the chosen configuration, prior to positioning the patient. Once the patient is in place, manually controlled adjustments to z-axis and α- and γ-axes rotations can be made, as described previously.

As previously described with reference to FIGS. 1-4, scanner 110 is configured to provide suitable travel paths for radiation source 22 and detector 24 about the extremity that is to be imaged, such as those shown in FIGS. 8-11. Scanner 110 operations in such various exemplary configurations can present a number of requirements that can be at least somewhat in conflict, including the following:

(i) Imaging over a large range of angles, preferably over an arc exceeding 180 degrees plus the fan angle of the radiation source.

(ii) Ease of patient access and extremity positioning for a wide range of limbs.

(iii) Capability to allow both weight-bearing and non-weight-bearing postures that allow imaging with minimized strain on the patient.

(iii) Enclosure to prevent inadvertent patient contact with moving parts.

(iv) Fixed registration of source to detector throughout the scan cycle.

Figure 12A:
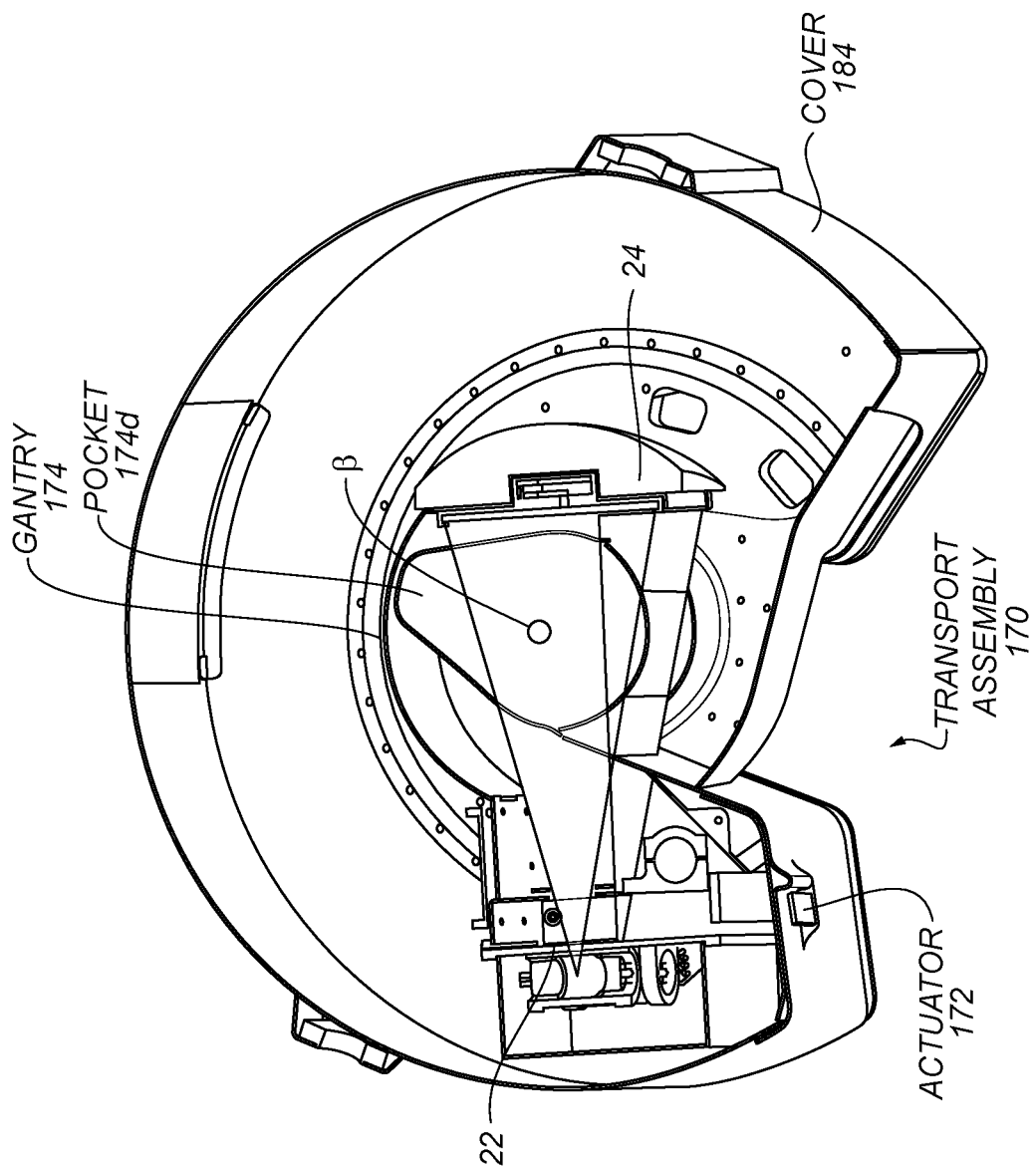
FIG. 12A is a top view of the scanner components of an extremity imaging apparatus according to an embodiment of the application.

The top view of FIG. 12A shows a configuration of components of scanner 110 that orbit subject 20 according to an exemplary embodiment of the application. One or more sources 22 and detector 24 are mounted in a cantilevered C-shaped gantry 174 that is part of a transport assembly 170 that can be controllably revolved (e.g., rotatable over an arc about central axis β). Source 22 and detector 24 are thus fixed relative to each other throughout their movement cycle. An rotary actuator 172, such as a motor, is mounted to a gantry 174 of assembly 170 and provides a moving hinge for gantry pivoting. Actuator 172 is energizable to move gantry 174 with clockwise (CW) or counterclockwise (CCW) rotation as needed for the scan sequence. Cover 184 can reduce or keeps out dust and debris and/or better protect the operator and patient from contact with moving parts.

Figure 12B:
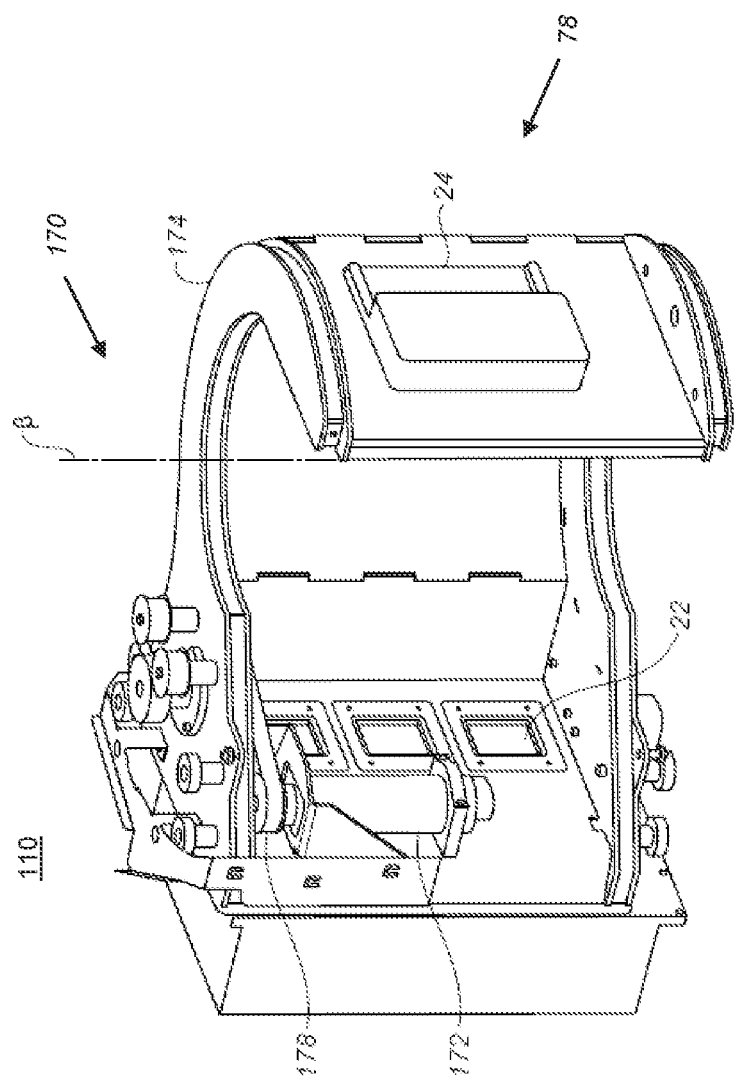
FIG. 12B is a perspective view of a frame that supports scanner components of an extremity imaging apparatus according to an embodiment of the application.

The perspective view of FIG. 12B shows gantry 174 of transport assembly 170 for scanner 110 in added detail. Actuator 172 cooperates with a belt 178 to pivot gantry 174 for moving source 22 and detector 24 about axis β.

Because a portion of the scan arc that is detector path 28 (FIG. 2) passes through the circumferential gap or opening 38 that allows patient access, this portion of the scan path should be isolated from the patient. FIGS. 13A and 13B show, in successive positions, for closing over gap or opening 38, a slidable door 176 that is stored in a retracted position within a housing for providing a covering over the detector path 28 once the patient is in proper position. In one embodiment, door 176 can be substantially a hollow structure that, when closed, allows passage of the detector 24 around the patient's extremity. Referring to FIG. 12B, the portion of gantry 174 that supports detector 24 can pass through the hollow inner chamber provided by door 176 during the imaging scan. At the conclusion of the imaging sequence, gantry 174 rotates back into its home position and door 176 is retracted to its original position for patient access or egress within housing 78. In one embodiment, the door 176 is manually opened and closed by the operator. In one embodiment, interlocks are provided so that movement of scanning transport components (rotation of cantilevered gantry 174) is only possible while full closure of the door 176 is sensed.

FIG. 13B also shows top and bottom surfaces 190 and 192, respectively, of housing 180. An outer circumferential surface 194 extends between and connects top and bottom surfaces 190 and 192. An inner circumferential surface 196 is configured to connect the top and bottom surfaces 190 and 192 to form a central opening 198 extending from the first surface to the second surface, where the central opening 198 surrounds the β axis.

As shown with respect to FIGS. 2 and 4, in one embodiment radiation source 22 and detector 24 each can orbit the subject along an arc with radii R2 and R1, respectively. According to an alternate embodiment, within source transport 32, a source actuator could be used, cooperating with a separate, complementary detector actuator that is part of detector transport 34. Thus, two independent actuator devices, one in each transport assembly, can be separately controlled and coordinated by an external logic controller to move source 22 and detector 24 along their respective arcs, in unison, about subject 20.

In the context of the present disclosure, a surface is considered to be "substantially" flat if it has a radius of curvature that exceeds about 10 feet.

The perspective view of FIG. 10 shows the extremity CBCT imaging apparatus 100 configured for knee imaging with a seated patient. From FIG. 10, it can be seen that the patient needs room outside of the scan volume for comfortable placement of the leg that is not being imaged. For this purpose, housing 78 is shaped to provide additional clearance.

As is readily visible from FIGS. 8-11 and 13A-13B, imaging scanner 110 has a housing 78. According to one embodiment of the application, housing 78 is substantially cylindrical; however, a cylindrical surface shape for housing 78 is not required. By substantially cylindrical is meant that, to at least a first approximation, the housing 78 surface shape closely approximates a cylinder, with some divergence from strict geometric definition of a cylinder and with a peripherally gap and some additional features for attachment and component interface that are not in themselves cylindrical.

Figure 14A:
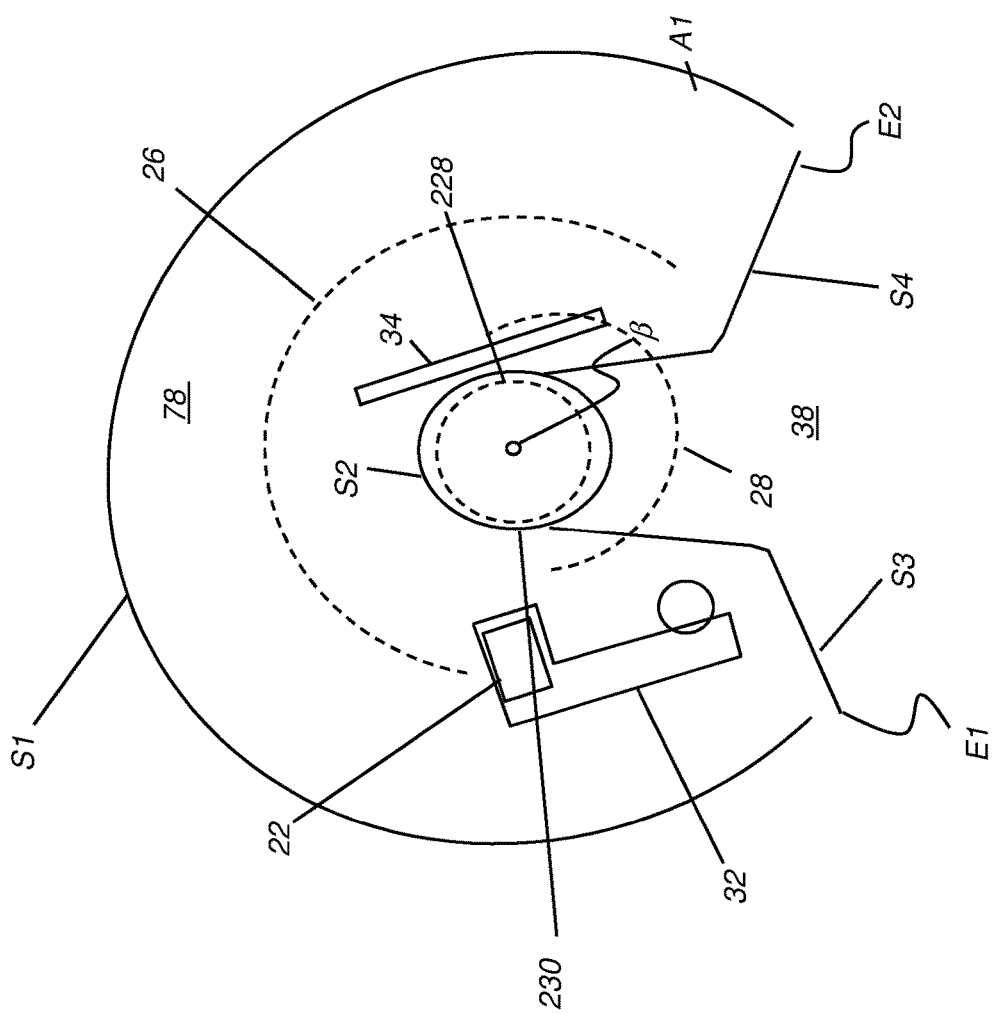
FIG. 14A is a top view of the imaging scanner with a number of its internal imaging components shown, at one extreme end of the imaging scan.
Figure 14B:
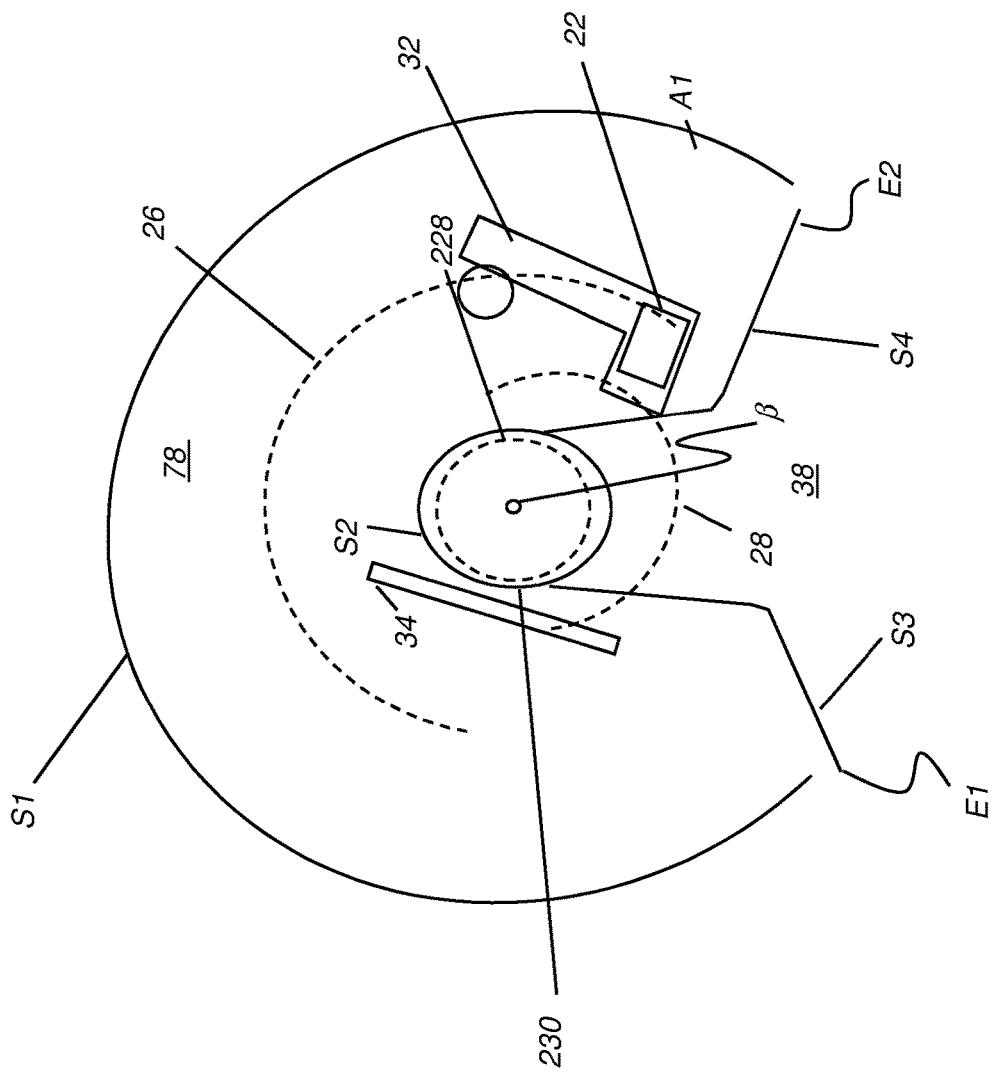
FIG. 14B is a top view of the imaging scanner with a number of its internal imaging components shown, at the opposite extreme end of the imaging scan from that shown in FIG. 14A.

FIGS. 14A-14C show a number of features that are of interest for an understanding of how scanner 110 is configured and operated (e.g., scans). FIG. 14A shows how peripheral gap 38 is formed by housing 78, according to an embodiment of the application. Scan volume 228, outlined with a dashed line, is defined by the source and detector paths 26 and 28, as described previously, and typically includes at least a portion of the β axis. An inner central volume 230 can be defined by surface S2 of housing 78 and can typically enclose scan volume 228. Inner central volume 230 can also be defined by door 176 when closed, as shown in FIG. 14C. Peripheral gap 38 is contiguous with inner central volume 230 when door 176 is in open position (e.g., fully or partially opened).

FIG. 14A shows source transport 32 and detector transport 34 at one extreme end of the scan path, which may be at either the beginning or the end of the scan. FIG. 14B shows source transport 32 and detector transport 34 at the other extreme end of the scan path. It should be noted that source 22 is offset along source transport 32. With this asymmetry, the extent of travel of source 22 relative to surface S3 of housing 78 differs from its extent of travel relative to surface S4. At the extreme travel position shown in FIG. 14B, source 22 is more than twice the distance from surface S4 as source 22 is from surface S3 at the other extreme travel position shown in FIG. 14A. In one embodiment, the inventors use this difference to gain additional clearance for patient positioning with the patient seated.

FIG. 14C shows the configuration of housing 78. In the context of the present disclosure, top surface 190 is considered to be aligned with the top of, at least partially above, or above scan volume 228; bottom surface 192 is aligned with the bottom of, at least partially below, or below scan volume 228. In one embodiment, the top surface 190 or the bottom surface 192 can intersect a portion of the scan volume 228. As shown in FIG. 14C, scan volume 228 can be cylindrical or circularly cylindrical. However, exemplary embodiments of the application are intended to be used with other known 2D scan areas and/or 3D scan volumes. The cover of housing 78 can be metal, fiberglass, plastic, or other suitable material. According to an embodiment, at least portions of top and bottom surfaces 190 and 192 are substantially flat.

As shown in FIGS. 14A-14C, the scanner 110 has a number of surfaces that define its shape and the shape of peripheral gap or opening 38:
 (i) an outer connecting surface S1 extends between a portion of top surface 190 and a portion of bottom surface 192 to at least partially encompass the source and detector; at least a portion of the outer connecting surface extends outside the path the source travels while scanning; embodiments of the outer connecting surface S1 shown in FIGS. 14A-14C provide an arcuate surface that is generally circular at a radius R5 about center β and that extends, between edges E1 and E2 of the housing;
 (ii) an inner connecting surface S2 extends between a portion of the first surface and a portion of the second surface to define an inner central volume 230 that includes a portion of scan volume 228;
 (iii) other connecting surfaces can optionally include a surface S3 that corresponds to a first endpoint of the travel path for source transport 32 (FIGS. 14A-14B) and is adjacent to curved surface S1 along an edge E1, wherein surface S3 extends inward toward curved inner surface S2; and a surface S4 that corresponds to a second endpoint at the extreme opposite end of the travel path from the first endpoint for source transport 32 and is adjacent to curved surface S1 along an edge E2 wherein surface S4 extends inward toward curved inner surface S2. According to an embodiment, surfaces S3 and S4 are substantially flat and the angle between surfaces S3 and S4 is greater than about 90 degrees. In general, other additional surface segments (e.g., short linear or curved surface segments) may extend between or comprise any of surfaces S1-S4.

Inner and outer connecting surfaces S1, S2, and, optionally, other surfaces, define peripheral gap or opening 38 that is contiguous with the inner central volume 230 and extends outward to intersect the outer connecting surface S1 to form gap 38 as an angular recess extending from beyond or toward where the outer connecting surface S1 would, if extended, cross the opening 38.

The needed room for patient anatomy, such as that described with reference to FIG. 10, can be provided when the central angle for arc A2 is large enough to accommodate the extremity that is to be imaged. According to one embodiment, the central angle for arc A2 between edges of gap 38 exceeds the central angle for arc A1 by at least about 5 degrees; more advantageously, the central angle for arc A2 exceeds the central angle for arc A1 by at least about 10 or 15 degrees.

The perspective views of FIGS. 8-11 show various configurations of extremity CBCT imaging apparatus 100 for imaging limbs of a patient. For each of these configurations, the limb or other extremity of the patient must be positioned at the center of scanner 110 and space must be provided for the paired extremity. As described herein, peripheral gap or opening 38 is provided to allow access space for the patient and room for other parts of the patient anatomy. Door 176 is withdrawn into the housing 78 until the patient is positioned; then, door 176 is pivoted into place in order to provide a suitable transport path for the imaging receiver, detector 24, isolated from the patient being imaged.

FIG. 13A shows scanner 110 with door 176 in open position, not obstructing opening 38, that is, keeping opening 38 clear, allowing patient access for extremity placement within opening 38.

According to one embodiment, the door 176 is manually pivoted, closed, and opened by the operator. This allows the operator to more carefully support the patient and the extremity that is to be imaged. According to an alternate embodiment, an actuator is provided to close or open the door automatically.

Figure 15:
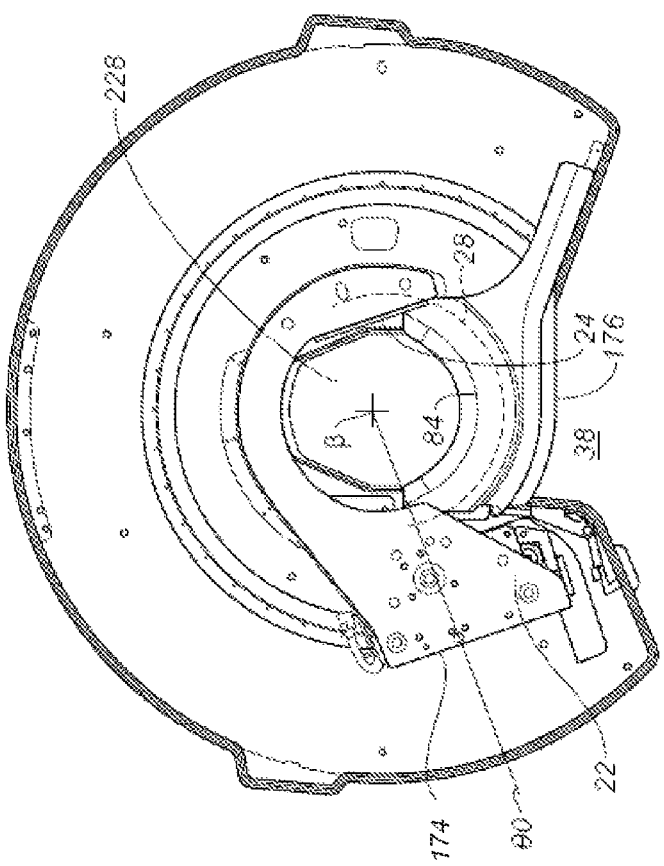
FIG. 15 is a top view that shows movement of scanning components that is allowable when the door of the scanner is closed.

FIG. 15 shows the initial position of gantry 174 at an angle θ0 when door 176 has just been closed. Source 22 and detector 24 are at a rest or default position at angle θ0. Detector path 28 extends into the hollow portion of door 176 as shown.

FIG. 15 shows, from a top view, the relative angular rotation of gantry 174 and how the hollow passage 84 provided by door 176 allows a wide angular range of travel for the orbit of detector 24 around the subject being imaged within the scan volume 228. This sequence shows how door 176 covers or surrounds, but does not obstruct, detector path 28 and shows how detector path 28 passes through the hollow interior of door 176 for imaging when the patient is appropriately positioned and door 176 is pivoted into place and latched. According to an alternate embodiment, another feature of door 176 is a closure portion 188 that can cover a door aperture 88 in housing 78 before, during and following door closing.

Figure 16:
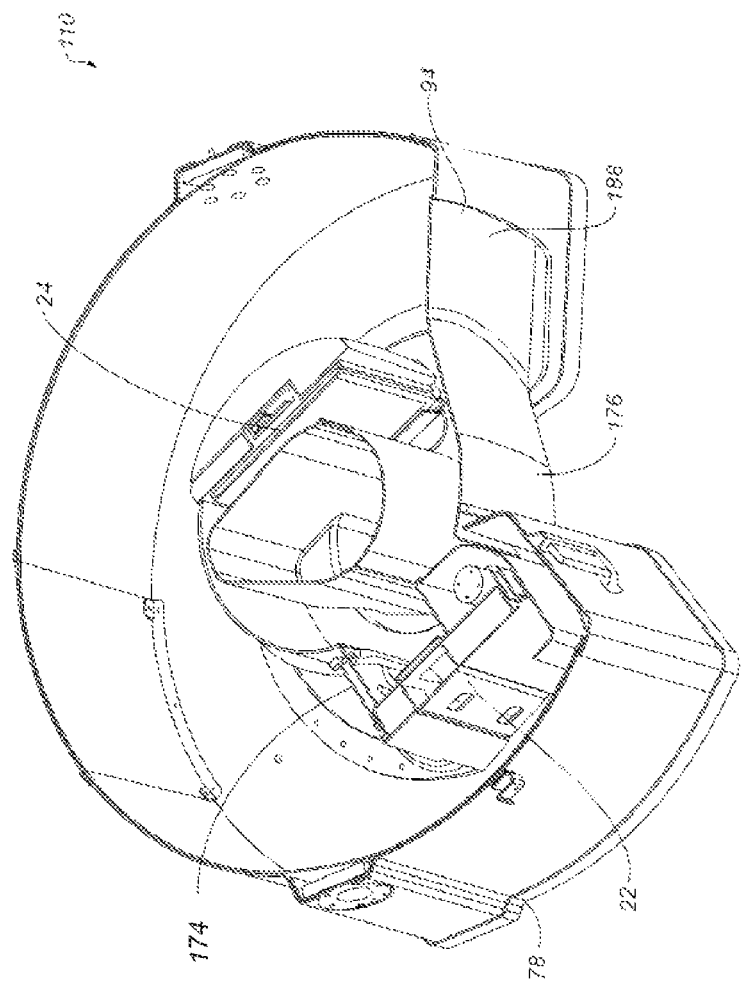
FIG. 16 is a perspective view of the scanner with the housing covers removed, showing the door in closed position.

The perspective view of FIG. 16, with the cover of housing 78 removed for visibility of internal parts, shows another feature of door 176. A closure portion 188 is provided as a part of door 176 to cover the gap that would otherwise be exposed when the door was closed. This covering keeps out dirt and debris and helps to prevent patient contact with, and visibility of, internal moving parts of scanner 110. According to an alternate embodiment, an edge 94 of closure portion 188 is attached to housing 78 and closure portion 188 folds or bends into place as door 176 pivots toward its closed position.

As shown in FIG. 6A, the source 22 and the detector 24 on the gantry 36 run on a portion of an arcuate non-linear guide rail (e.g., slot). However, the mass of a radiation source can be 5×, 10×, 20× or more relative to the mass of a radiation detector. In exemplary CBCT X-ray imaging systems, the combination of the uneven source 22 and detector 24 masses and/or the position of the masses relative to a scanning volume or a center of rotation (e.g., β axis) can create a large imbalance. For example, the unbalanced CBCT gantry mechanism can suffer backlash when the source "tips over" a high position (or low position) of tilted scan geometry.

Figure 17A:
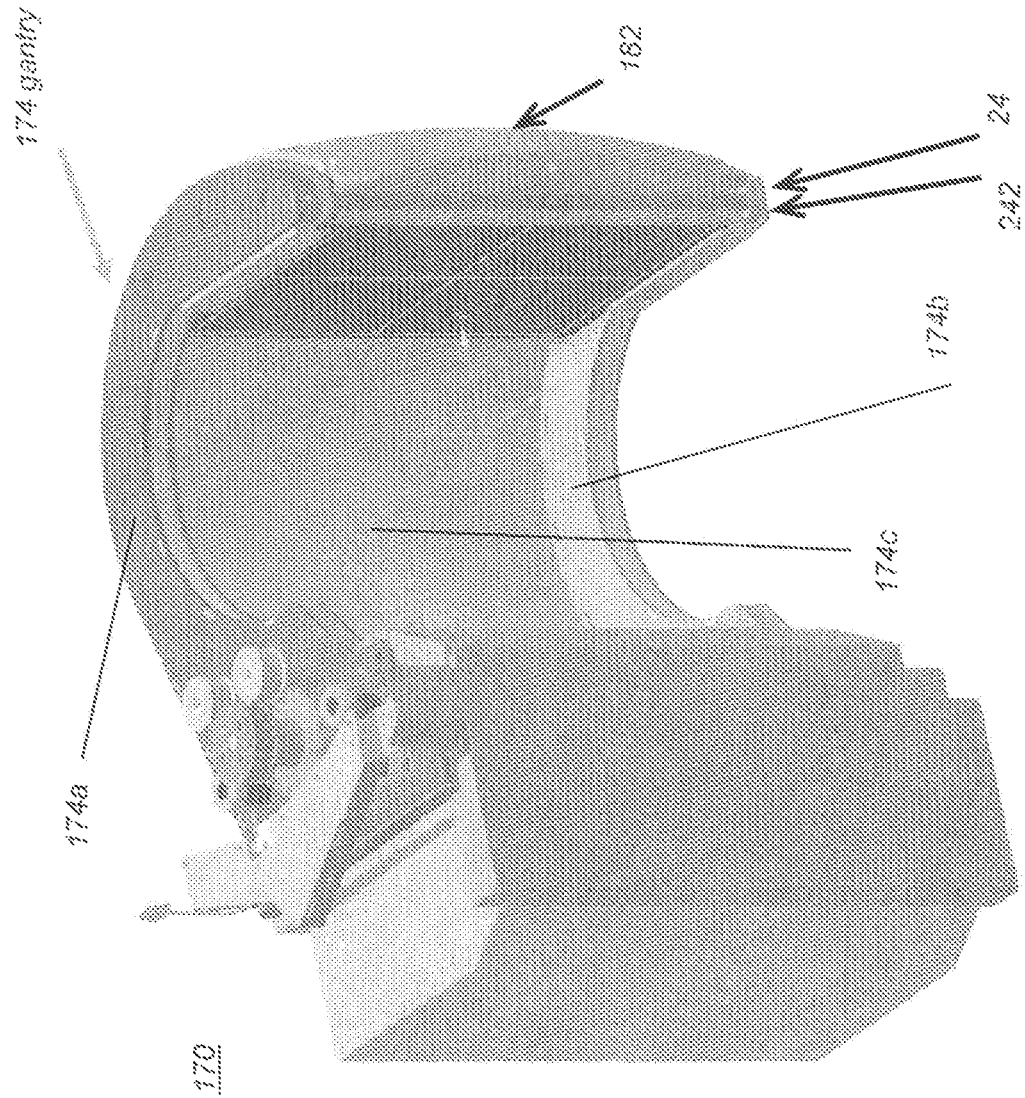
FIGS. 17A and 17B are diagrams that show additional features of exemplary gantry and/or transport mechanism for use in CBCT X-ray imaging systems.
Figure 17B:
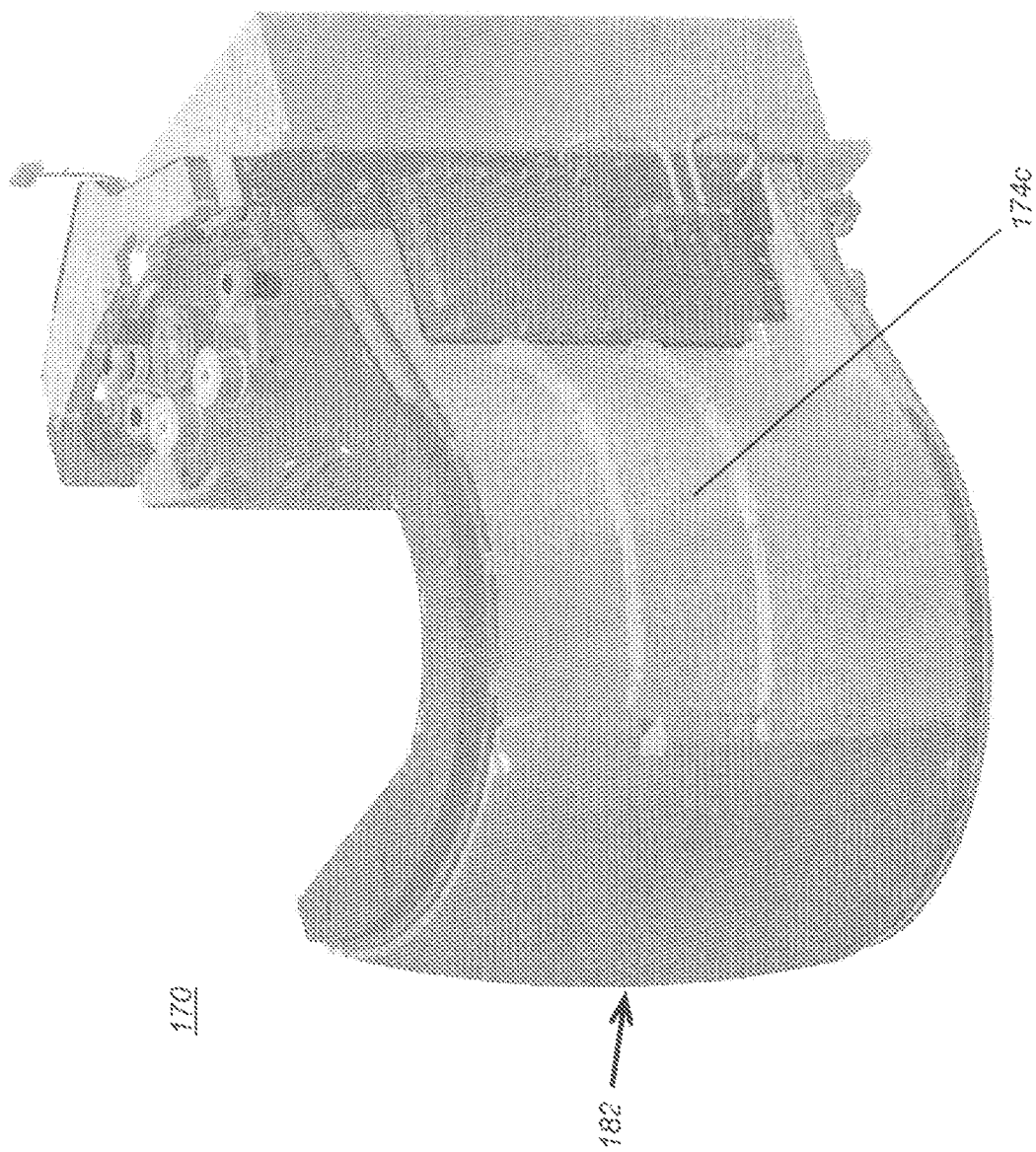
Figure 18A:
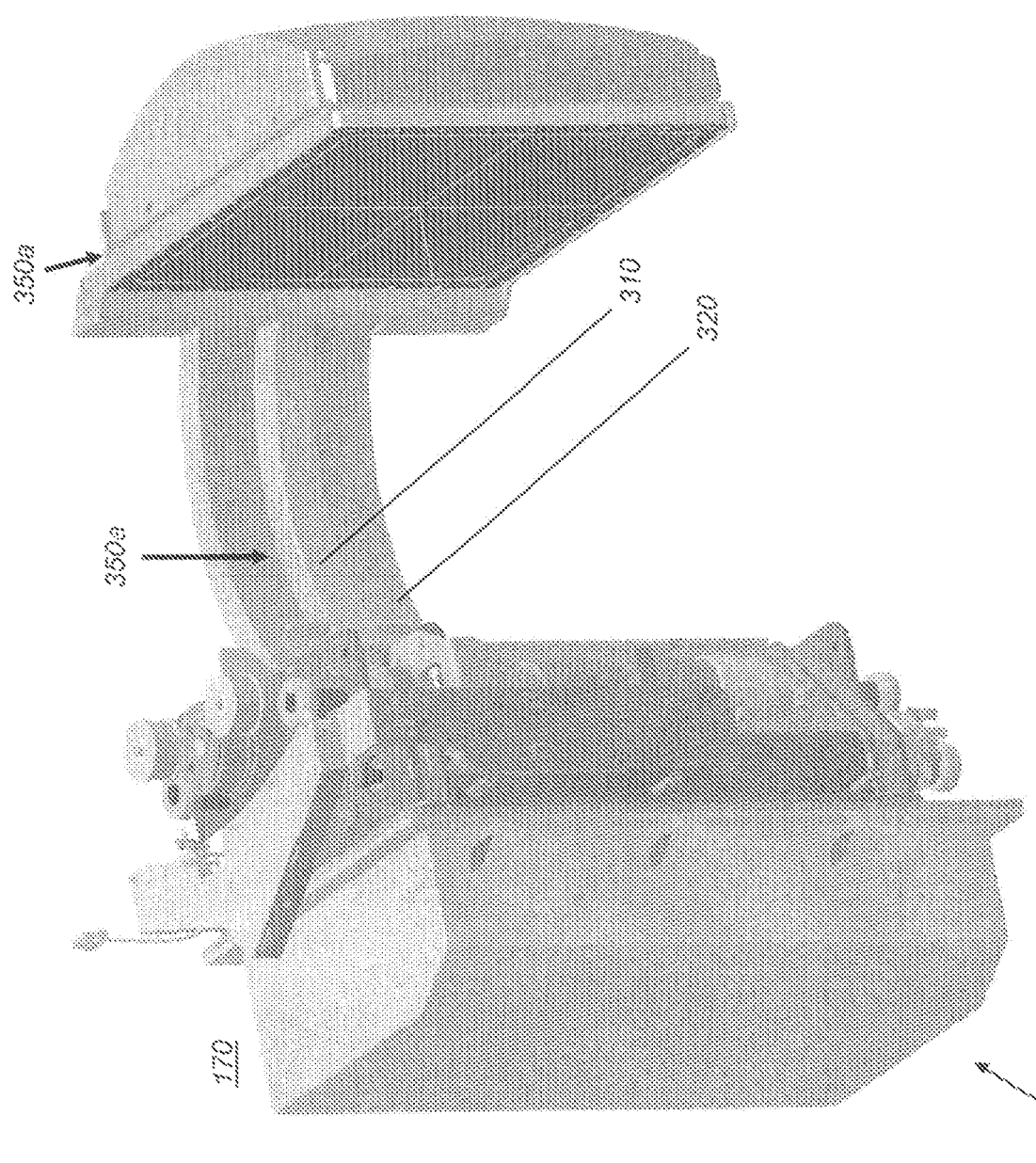
Figure 18B:
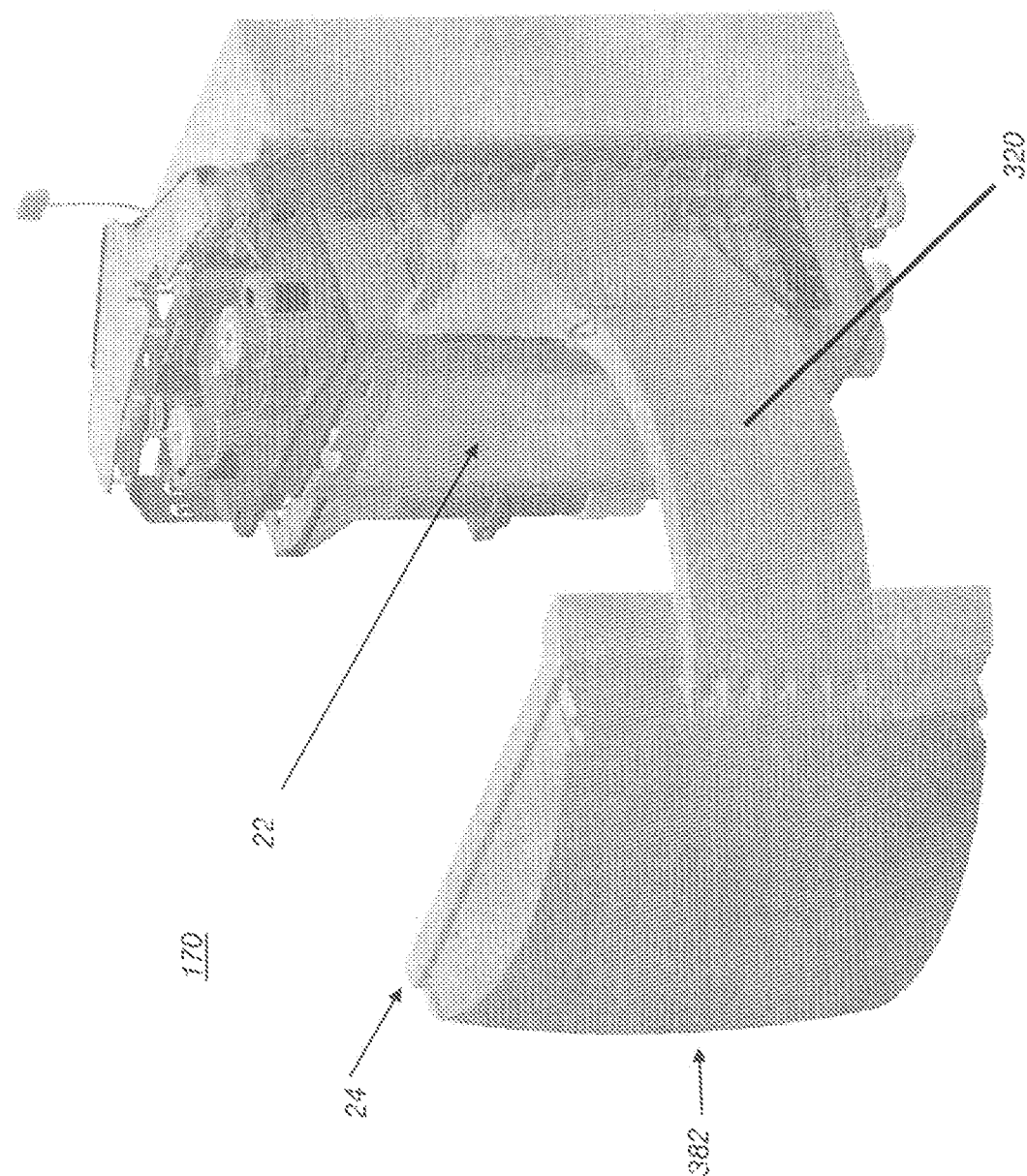
Figure 18D:
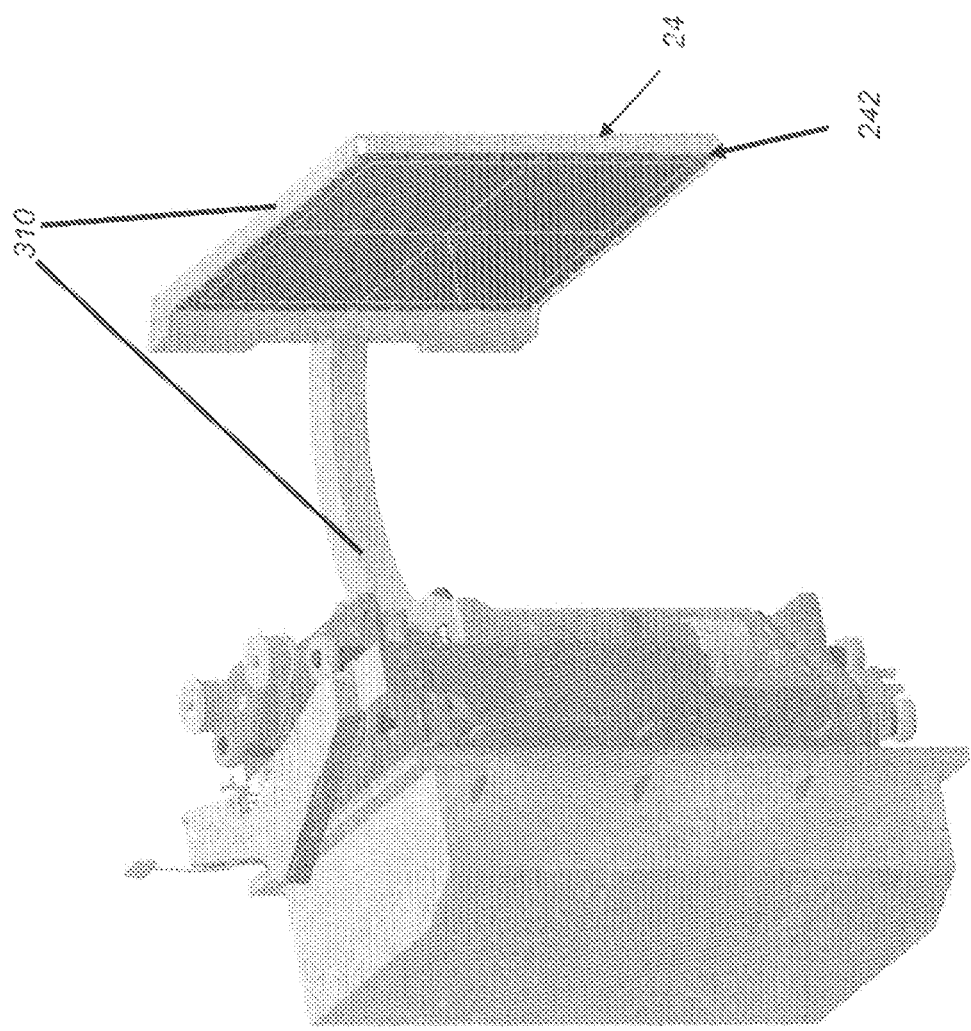

Accordingly, a counterweight can be added to a detector to move the center of gravity (COG) of a scanner (e.g., scanner 110 or gantry 174) closer to the scanning volume or center of rotation and/or to reduce the mass imbalance of the source and detector. FIGS. 17A and 17B show the counterweight 182 added to the detector 24. A counterweight being added to a detector can provide advantages for motion control such as but not limited to (i) a force to drive the counter-balanced gantry in all orientations can be reduced, (ii) inertia can be increased and can be more easily controlled and/or (iii) vibration (e.g., between the source and detector) during motion or scanning of the scan volume can be reduced.

A counterweight can include disadvantages to CBCT X-ray imaging systems and/or methods with the more balanced gantry. Preferably, the source 22 and the detector 24 do not move relative to one another during scanning of the scan volume 228. Accordingly, a very strong structure is needed to withstand the bending forces created and/or applied to a gantry 174 by the counterweight 182 (and/or source 22, detector 24). Further, the structure must be sufficient to move the radiation source and detector (with counterweight) in unison.

FIGS. 17A and 17B are diagrams that show additional features of portions of a gantry for a transport assembly 170 for use in CBCT X-ray imaging systems. As shown in FIGS. 17A and 17B, the gantry 174 of the transport assembly mechanism 170 can use a massive integrated structure to withstand the bending forces created and/or applied by the counterweight 182, the detector 24 and/or the source 22. Further, the gantry 174 can include first or top portion 174a, second or lower portion 174b that extend toward or into the scan volume 228, which can be connected by frame connecting portion 174c. In one embodiment, the portion 174a, the portion 174b, and the portion 174c, can form an interior pocket 174d (see FIG. 12A) extending at least partially between the portion 174a and the portion 174b. FIG. 17B shows an exterior surface of the gantry 174. As shown in FIGS. 17A and 17B, the gantry 174 can be integrally formed, integrated affixed in sections, rigidly connected or the like.

In one embodiment, a detector can include a grid, which can be integral or removably attached. As shown in FIGS. 17A and 17B, in its position against the detector 24 along the detector path, exemplary grid 242 is constrained for six degrees of freedom (DOF).

Certain exemplary embodiments of X-ray imaging systems (e.g., volume radiographic imaging systems, CBCT systems) and/or methods for using the same can provide a detector and a counterweight separately (e.g., scanner or gantry) even though the counterweight and detector can be positioned in or traverse the same relative space. In one embodiment, X-ray imaging systems and/or methods can provide a detector and a counterweight near distal ends of separate support arms (e.g., first and second support arms or a detector weight support unit with a counterweight support unit). In other embodiments, a detector and counterweight can be coupled to a gantry mechanism or transport mechanism (e.g., of a scanner) and configured to move independently from one another.

In certain exemplary embodiments, imaging systems (e.g., CBCT systems) can provide two separate supports individually for a detector and a counterweight. Further, separate supports structures can provide the ability to position the detector relative to the source during scanning with reduced or minimal movement or vibration. In certain exemplary embodiments, a weaker, lighter, smaller, different material and/or more flexible support for the counterweight can reduce the total weight of materials from that used to position and support the detector and the counterweight as a single unit. Further, separate supports can allow positioning of the counterweight proximate the detector path while allowing independent motion with increased vibration of the counterweight during scanning that has reduced impact or minimal impact on the quality of the diagnostic radiographic imaging or imaging data obtained. In addition, providing two separate supports individually for a detector and a counterweight can allow different materials (e.g., with different characteristics such as but not limited to density, strength, rigidity, resistance to bending, cost or the like) to be used for respective support structures for the detector and the counterweight.

FIGS. 18A-18D are diagrams that show an exemplary embodiment of a counterweight support mechanism for use with a gantry for a transport mechanism for use in radiographic imaging systems (e.g., CBCT X-ray imaging systems) and/or methods for using the same. As shown in FIGS. 18A-18D, two separate supports can include a detector weight support arm 310 coupled to support the detector 24 and a counterweight support arm 320 (e.g., separate and individually provided) coupled to support a counterweight 382. In certain exemplary embodiments, the detector weight support arm 310 and the counterweight support arm 320 can be made from different materials or combinations of materials. As shown in FIGS. 18A-18D, the detector weight support arm 310 and the counterweight support arm 320 can be coupled at first ends to a gantry 336 and at second (or distal) ends coupled to the detector 24 and the counterweight 382, respectively. In certain exemplary embodiments, the detector weight support arm 310 and the counterweight support arm 320 are separated by a first clearance gap 350a. In one embodiment, the detector 24 and the counterweight 382 can be separated by a second clearance gap. Preferably, the detector weight support arm 310 and the counterweight support arm 320 can extend circumferentially around without impinging the scan volume. In one embodiment, the counterweight support arm 320 can include a curved shape of a C-arm or other curved extensions between its mount to the gantry 336 and the counterweight 382. As shown in FIGS. 18A-18D, the detector weight support arm 310 can be positioned inside (e.g., radially or relative to the scan volume) the counterweight support arm 320. Preferably, the source 22 is also mounted to the gantry 336 (or other portion of a transport mechanism). In one embodiment, one or more sources 22 and the detector 24 can be mounted in the gantry 336 that is part of a transport assembly that can be controllably revolved (e.g., rotatable at least partially about a scan volume or axis β).

In certain exemplary embodiments of transport assembly 170, the counterweight support arm 320 can have any prescribed 3D shape to attach the counterweight 382 to the scanner without crossing the scan volume 228. For example, the counterweight support arm 320 can include the shape of a C-arm or an arcuate extension between a source mount at the gantry and the counterweight. Alternatively, a counterweight support arm can include a curved or non-linear shape between a mount connection to the gantry mechanism and a mount connection to the counterweight. In other embodiments, the counterweight support arm can include a series of linear sections that together form a prescribed form between the gantry mechanism and the counterweight. Any configuration (e.g., mechanical or electro-mechanical) is envisioned that locates the counterweight in the intended position physically separated from the detector, which is mounted to receive radiation from the source across an opening or scan volume. In one embodiment, the detector weight support mechanism and the counterweight support mechanism have similar (or identical) shapes. In one embodiment, a detector weight support mechanism and a counterweight support mechanism have similar sickle shapes. In one embodiment, the detector weight support mechanism or the counterweight support mechanism can include a form that crosses below or above the scan volume. In one embodiment, the detector weight support mechanism or the counterweight support mechanism can have similar shapes that encircle the scan volume.

In certain exemplary embodiments, the detector weight support arm 310 is configured to limit the detector 24 motion during scanning of the scan volume 228 to less than ½, ⅓ or ⅟₁₀ of the motion of the counterweight 382 allowed by the counterweight support arm 320 during scanning of the scan volume 228. In one embodiment, the detector weight support arm 310 can connect the detector 24 to the source 22 (e.g., gantry 336) such that less than 5 mm, less than 3 mm or less than 1 mm of motion is created at the detector 24 (e.g., or relative motion between the source 22 and the detector 24) during scanning of the scan volume 228. In one embodiment, the counterweight support arm 320 connects the counterweight 382 to the source 22 (e.g., gantry 336) such that less than 12 mm, less than 8, or less than 3 mm of motion is created at the counterweight 382 during scanning of the scan volume 228. In one embodiment, the detector weight support arm 310 can secure the detector 24 to a gantry mechanism with reduced movement as compared to known configurations where the detector and counterweight move and/or are mounted as a single unit (e.g., using gantry 174).

In certain exemplary embodiments, providing two separate supports individually for a detector and a counterweight can provide the ability to provide a prescribed size clearance gap between the detector and the counterweight. In one embodiment, the clearance gap can be a preset 3-dimensional gap, a 2-dimensional gap or a distance between the detector weight support arm 310 and the counterweight support arm 320 (or between the detector 24 and the counterweight 382). In one embodiment, a clearance gap can be set responsive to (e.g., proportional, weighted, non-linear) to the amount of calculated movement (e.g., deflection) and/or actual movement of the counterweight 382 during scanning of the scan volume 228 or during any movement of a CBCT radiographic imaging system. In one embodiment, a clearance gap can be set responsive to (e.g., proportional, weighted, non-linear) to the amount of calculated movement (e.g., deflection) and/or actual movement of the detector 24 (source movement, relative movement between detector and source, scanner, etc.) during scanning of the scan volume 228 or during any movement of the CBCT radiographic imaging system.

In certain exemplary embodiments, providing two separate supports individually for the detector and the counterweight can provide increased bore size and/or increased scan volume of a CBCT radiographic imaging system. In certain exemplary embodiments, providing two separate supports individually for the detector 24 and the counterweight 382 can provide the ability to increase a bore size and/or increase a scan volume of a CBCT radiographic imaging system. Preferably, while maintaining or reducing calculated or actual movement between the source 22 the detector 24 during scanning of the scan volume 228.

Figure 19A:
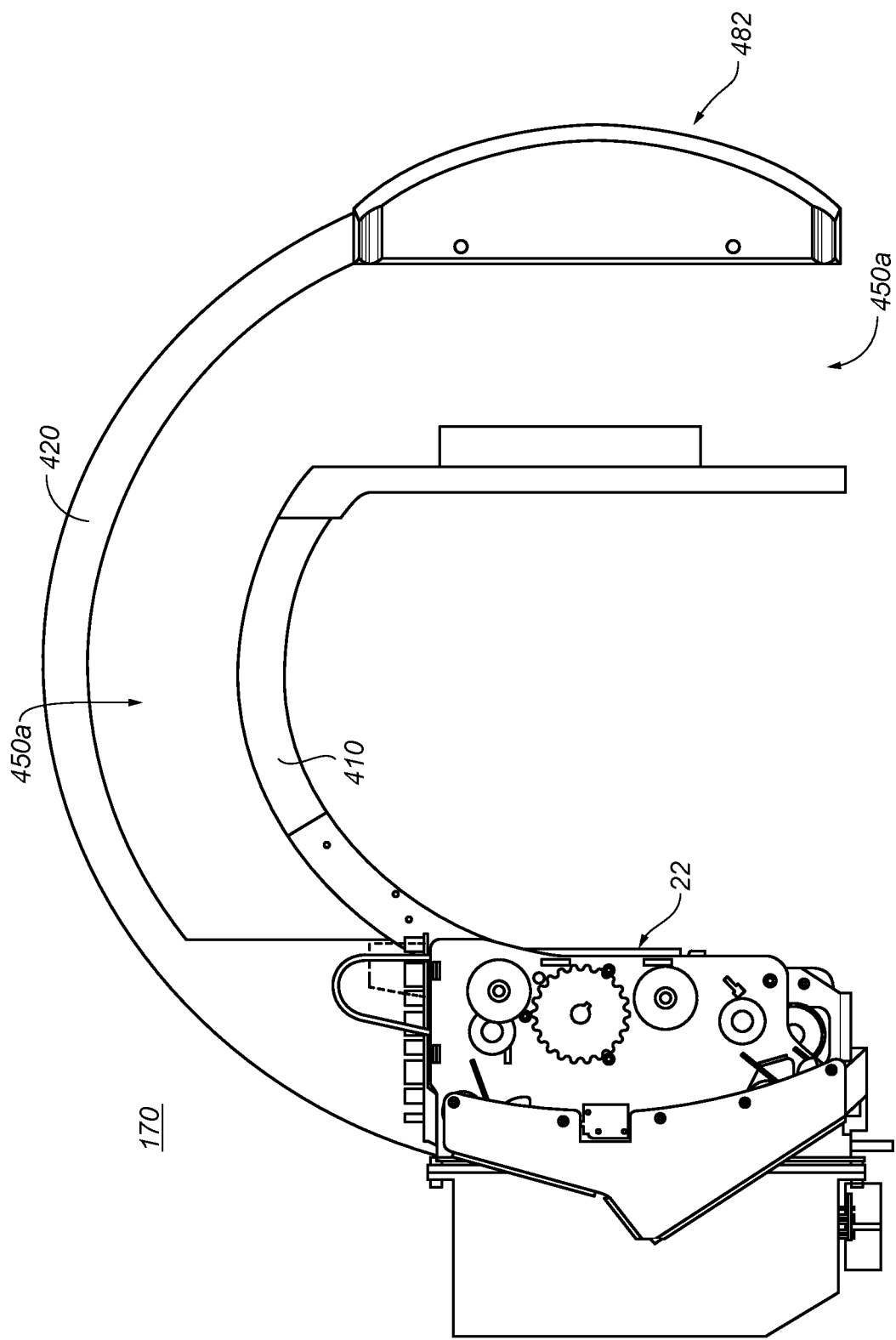
FIGS. 19A-19B are diagrams that show an exemplary embodiment of a counterweight support mechanism for use with a gantry for a transport mechanism for use in CBCT radiographic imaging systems or the like according to the application.
Figure 19B:
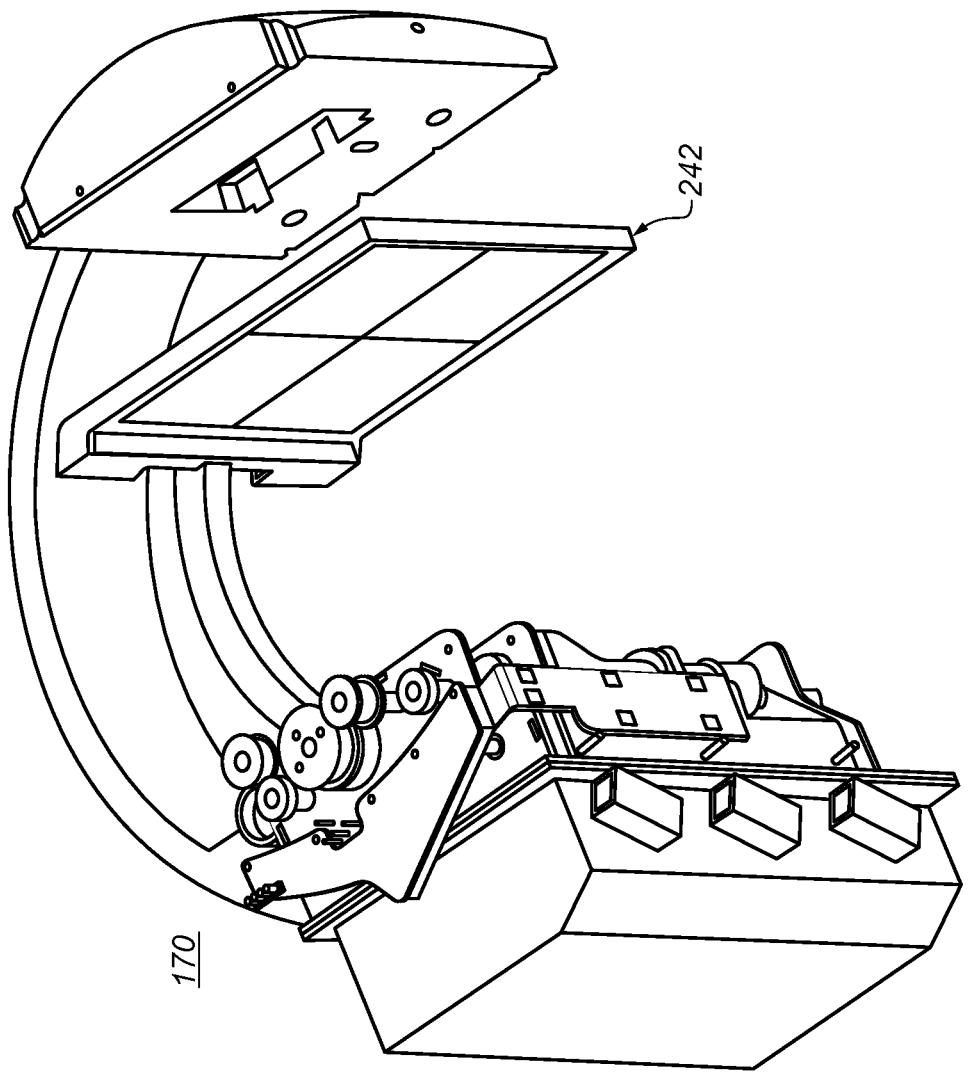

FIGS. 19A-19B are diagrams that show an exemplary embodiment of a counterweight support mechanism for use with a gantry for a transport mechanism for use in CBCT radiographic imaging systems or the like. As shown in FIGS. 19A-19B, two separate supports can include a detector weight support arm 410 coupled to support the detector 24 and counterweight support arm 420 (e.g., separate and individually provided) coupled to support a counterweight 482. As shown in FIGS. 19A-19B, the detector weight support arm 410 and the counterweight support arm 420 can be coupled at first ends to a gantry and at second (or distal) ends coupled to the detector 24 and the counterweight 482, respectively. In certain exemplary embodiments, the detector weight support arm 410 and the counterweight support arm 420 are separated by a first clearance gap 450a. In one embodiment, the detector 24 and the counterweight 482 can be separated by a second clearance gap. Preferably, the detector weight support arm 410 and the counterweight support arm 420 can extend outside or circumferentially around without impinging upon the scan volume. As shown in FIGS. 19A-19B, the detector weight support arm 410 can be positioned inside (e.g., radially or relative to the scan volume) the counterweight support arm 420 so that a paired extremity can pass therebetween. Preferably, the source 22 is also mounted to the gantry 336.

Figure 20:
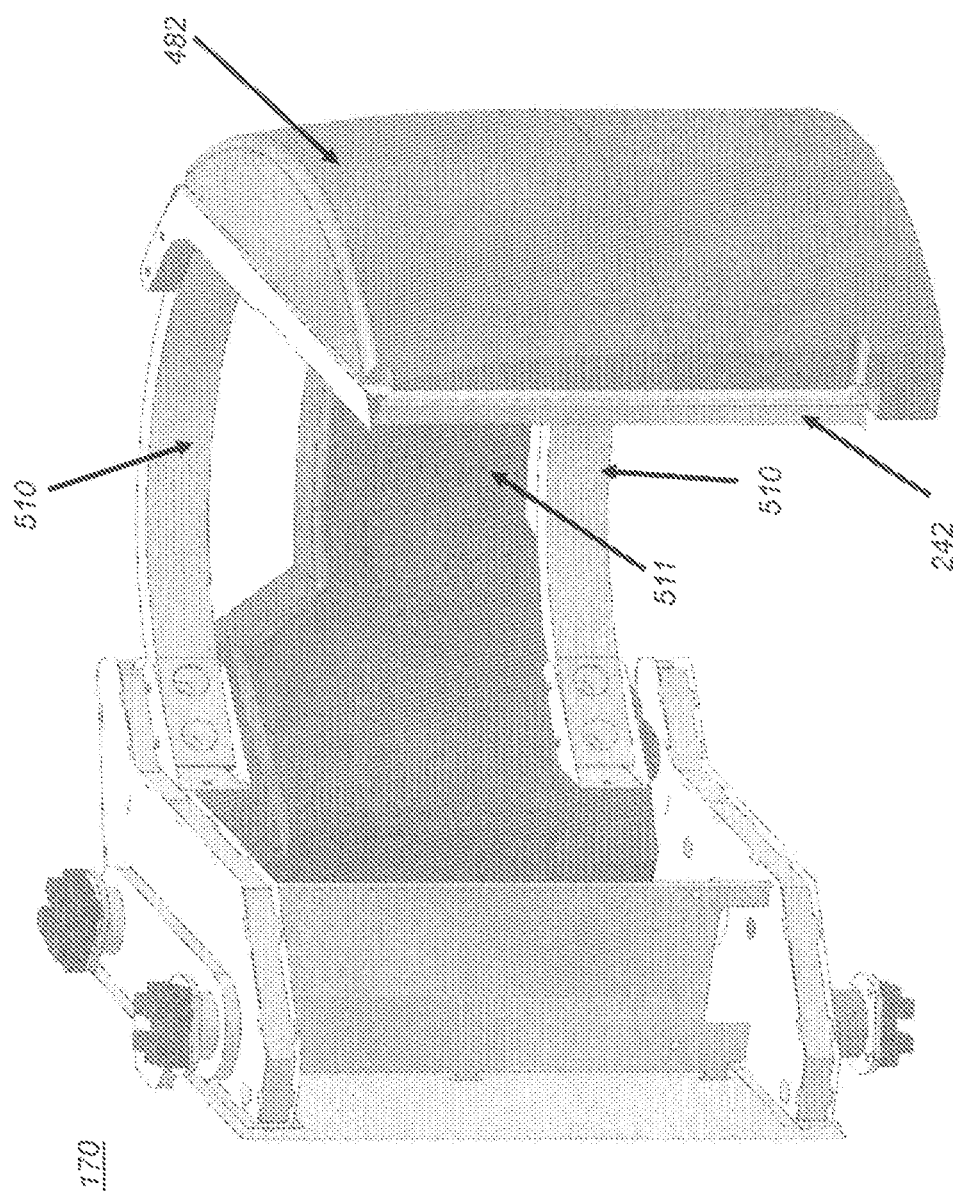
FIGS. 20-21 are diagrams that show an exemplary embodiment of a counterweight support mechanism for use with a gantry for a transport mechanism for use in CBCT radiographic imaging systems or the like according to the application.
Figure 21:
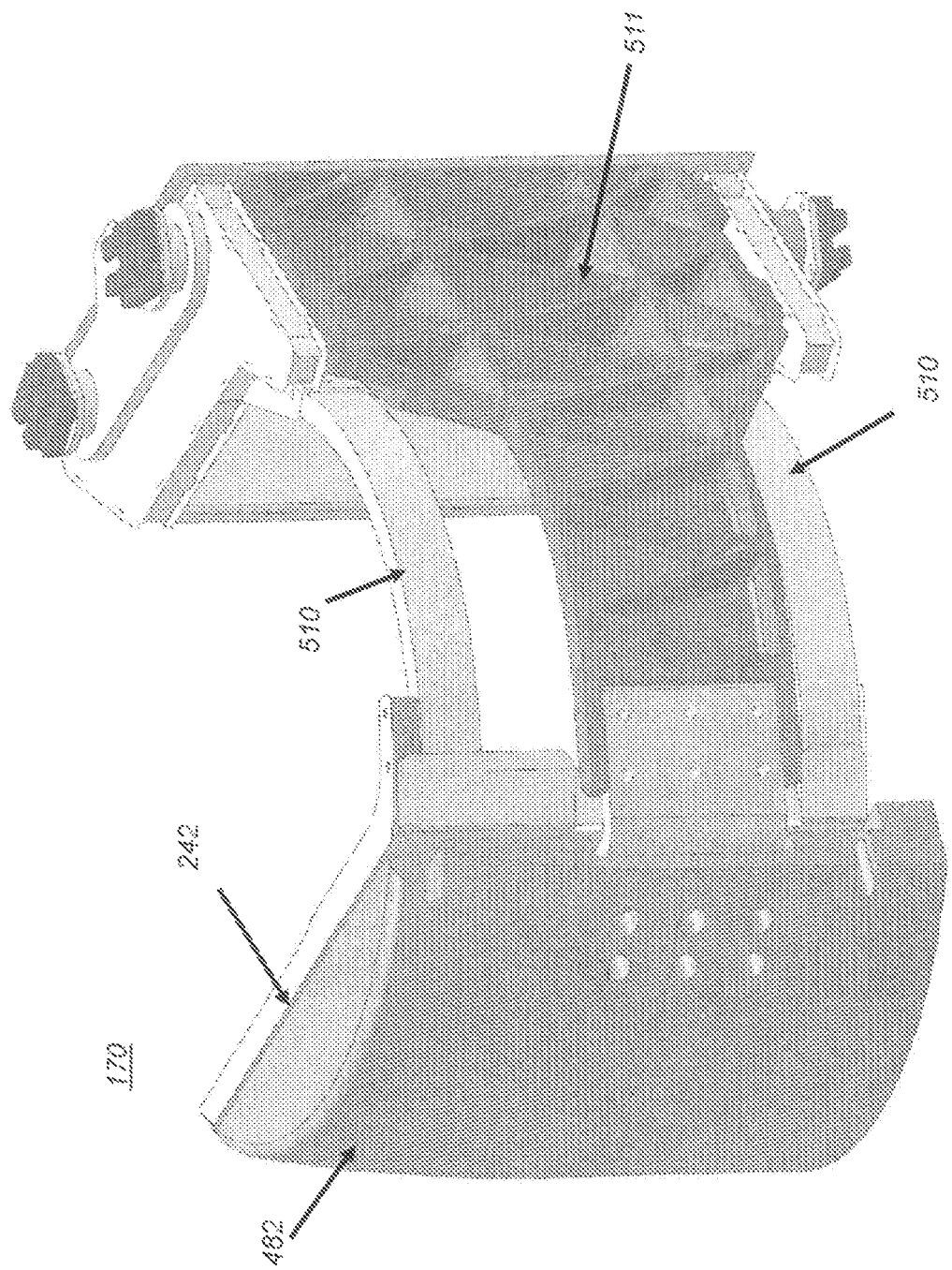

FIGS. 20-21 are diagrams that show an exemplary embodiment of a counterweight support mechanism for use with a gantry for a transport assembly 170 mechanism for use in CBCT radiographic imaging systems or the like. As shown in FIGS. 20-21, two separate supports can include detector weight support arms 510 coupled to support the detector 24 and counterweight support arm 511 coupled to support a counterweight 482. As shown in FIGS. 20-21, detector weight support arms 510 and/or the counterweight support arm 511 can be formed as a plurality of support arms/units (e.g., mechanically or electro-mechanically connected or separated) coupled at one or more first ends to a gantry and at one or more second (or distal) ends coupled to the detector 24 and the counterweight 482, respectively.

In certain embodiments, a detector weight support arm 510 and/or a counterweight support arm 511 are shown as separate units that are attached to the gantry 174 (or scanner 110). In alternative exemplary embodiments, detector weight support arm and/or a counterweight support arm can be integrally formed as a single unit with one or more portions of a transport mechanism (e.g., gantry 174) or a scanner 110.

Radiographic imaging systems typically use a linear grid as an anti-scatter device that improves contrast and signal to noise (S/N) ratio in radiographic images. A grid typically includes a series of lead foil strips that block x-rays separated by spacers that are transmissive to x-rays. The spacing of the strips determines the grid frequency, and the height-to-distance between lead strips determines a grid ratio. These and other grid characteristics can vary depending on the radiation energy that is used for a particular image. Calibration of the detector takes grid characteristics into account, so that different calibration data are used for different grids. In certain exemplary embodiments herein, a detector can include a grid, which can be integral or removably attached to the detector. Certain exemplary embodiments according to the application can provide grid access (e.g., through door 176) for replacement with a different grid or removal of the grid from the imaging path.

The counterweight support mechanism previously described can have considerable mass, with weight exceeding 250 lbs. As the imaging apparatus orbits the detector and source about the patient in an imaging sequence, the shifting of this mass exerts significant forces on various portions of the supporting structure. The problem of moving and supporting this mass while maintaining precise registration is significant. It can be appreciated that it is at best impractical to construct a transport system with perfectly manufactured components and assembly tolerances, and with support structures unaffected by changes in component movement. Moreover, the need to orient the scanner at different heights and angles for different exams, as outlined hereinabove, significantly complicates the difficulty of maintaining registration and transport without some amount of distortion and component binding, such as binding of roller bearings.

Figure 22:
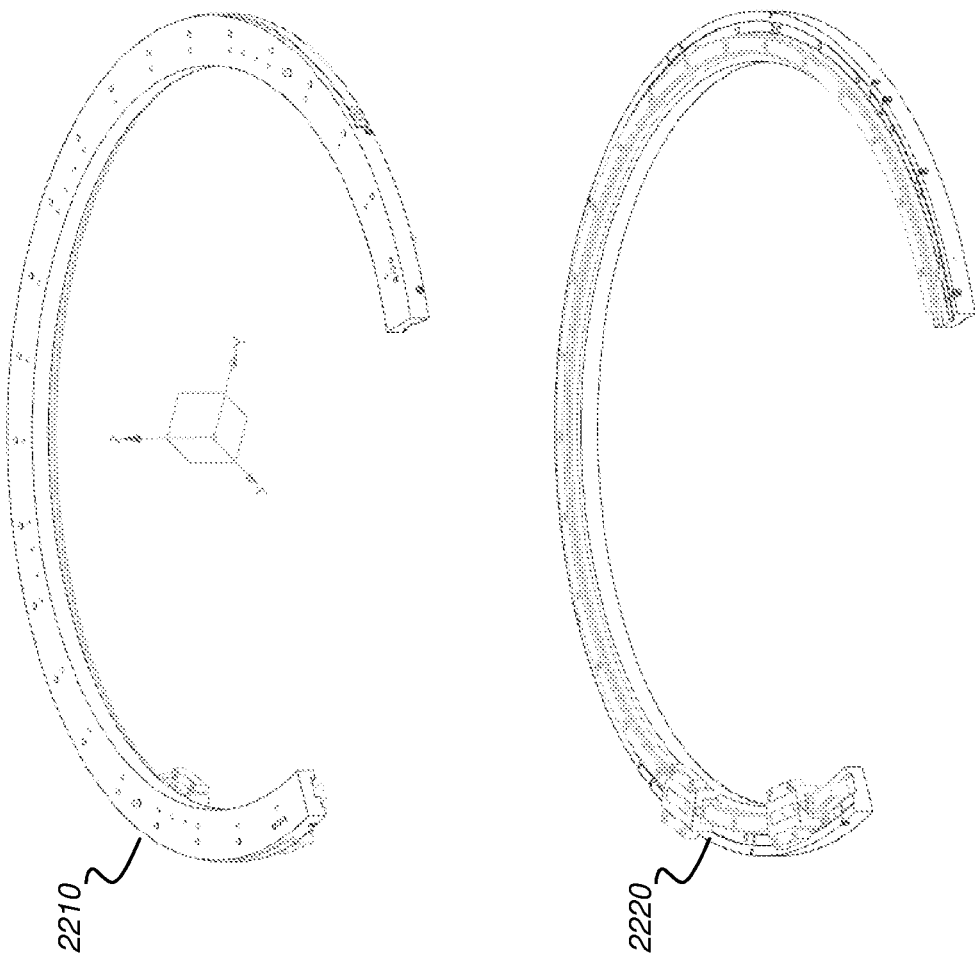
FIG. 22 is a perspective diagram that shows upper and lower rails that define a transport path for the transport assembly.

The perspective view of FIG. 22 shows upper and lower guide rails 2210 and 2220 that are mounted within the scanner 110 and define the arcuate transport path of transport assembly 170 for source and detector components, counterweight components, and related gantry components.

Figure 23:
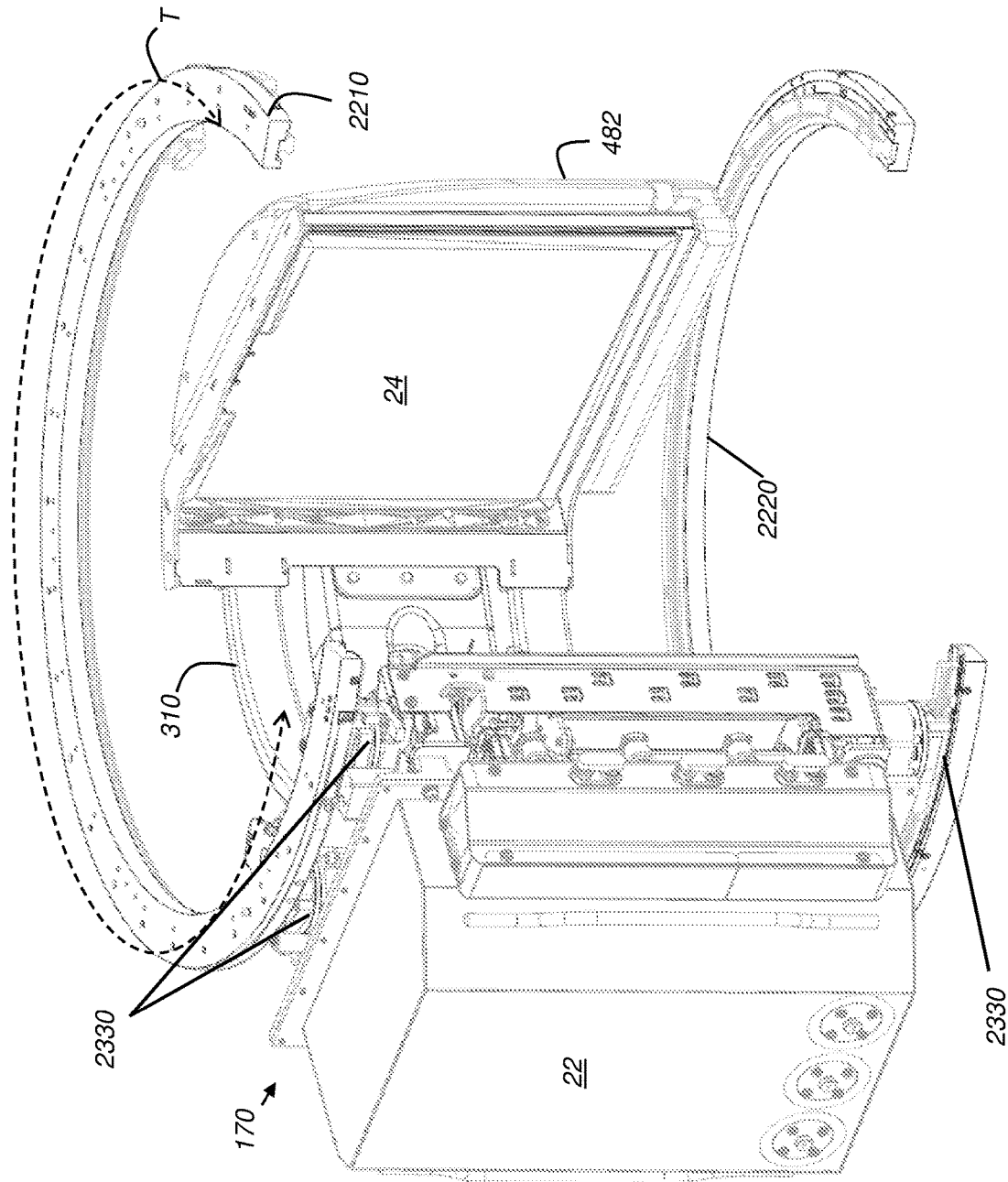
FIG. 23 is a perspective diagram that shows the transport assembly configured for transport along the path defined by upper and lower rails.

The perspective view of FIG. 23 shows transport assembly 170 with its associated source, detector, and counterweight components located at a start position along the transport path T and configured for transport between guide rails 2210 and 2220. Bearing carriages 2330 (also referred to herein as a slidable mounting plate) guide and support transport assembly 170 movement along the transport path T defined by rails 2210, 2220. Three of four bearing carriages 2330 are shown in the perspective view of FIG. 23 and in the plan view of FIG. 24.

Figure 24:
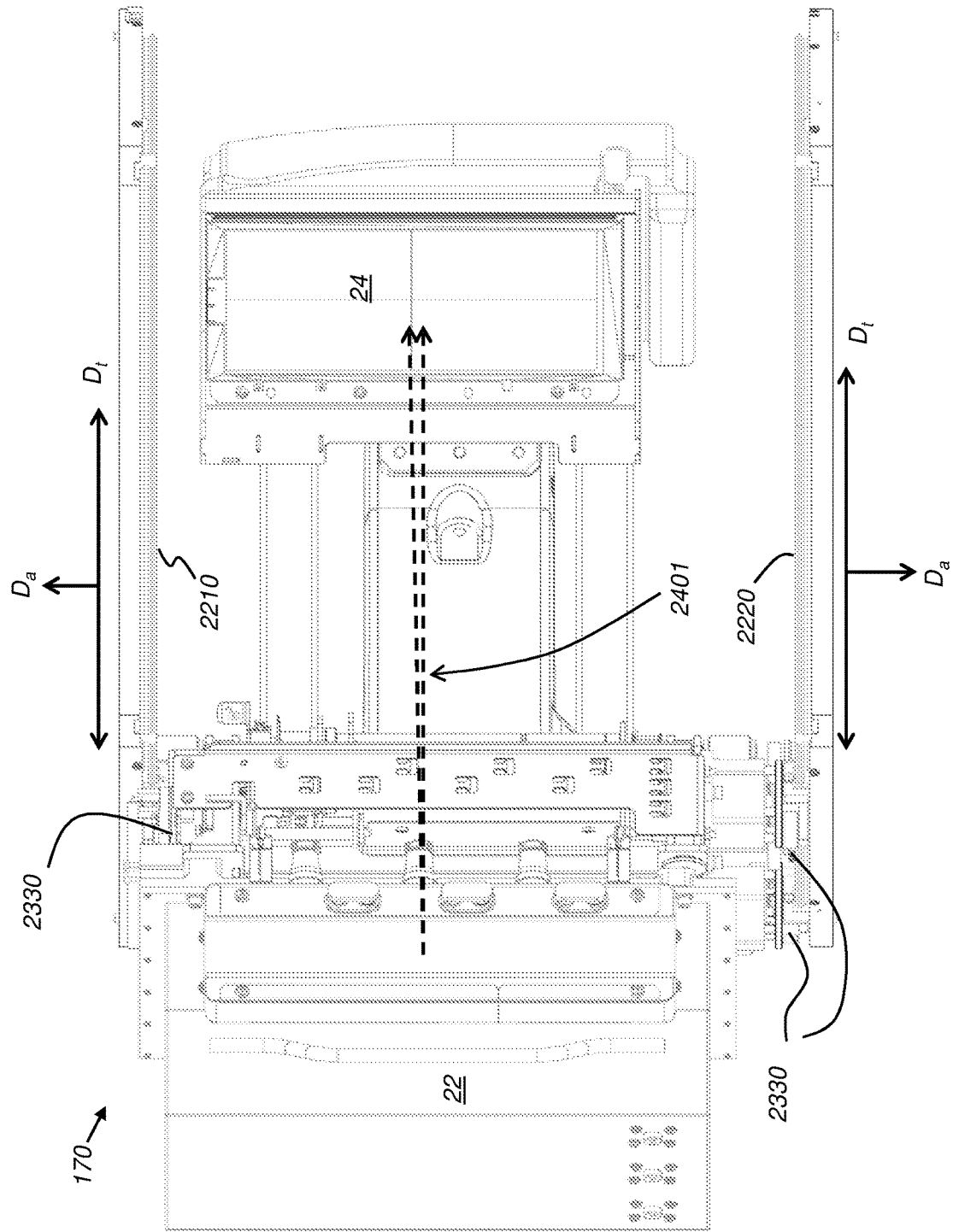
FIG. 24 is a plan view that shows the position of bearing carriage components along the transport assembly.

In order to address the problem of potential rail misalignment due to weight shifting, the Applicants employ paired gimbaled spherical joints in a configuration that compensates for slight changes in alignment between upper and lower rails 2210 and 2220. The plan view of FIG. 24 shows a transport direction $D_t$ for transport assembly 170 along curved rails 2210 and 2220 and an axial direction $D_a$ parallel to an imaging axis of the source and detector 22, 24, that is perpendicular to the transport direction $D_t$. As the dashed lines 2401 represent, variation in rail alignment can cause some slight amount of shift in the angle of the x-rays emitted by the source 22, thereby affecting acquired content of radiographic images captured by detector 24. However, this problem can be corrected by profiling transport assembly 170 movement and imaging characteristics using geometric calibration techniques. Embodiments of the present disclosure are directed to correcting the transport mechanics to reduce bearing wear and binding.

Figure 25:
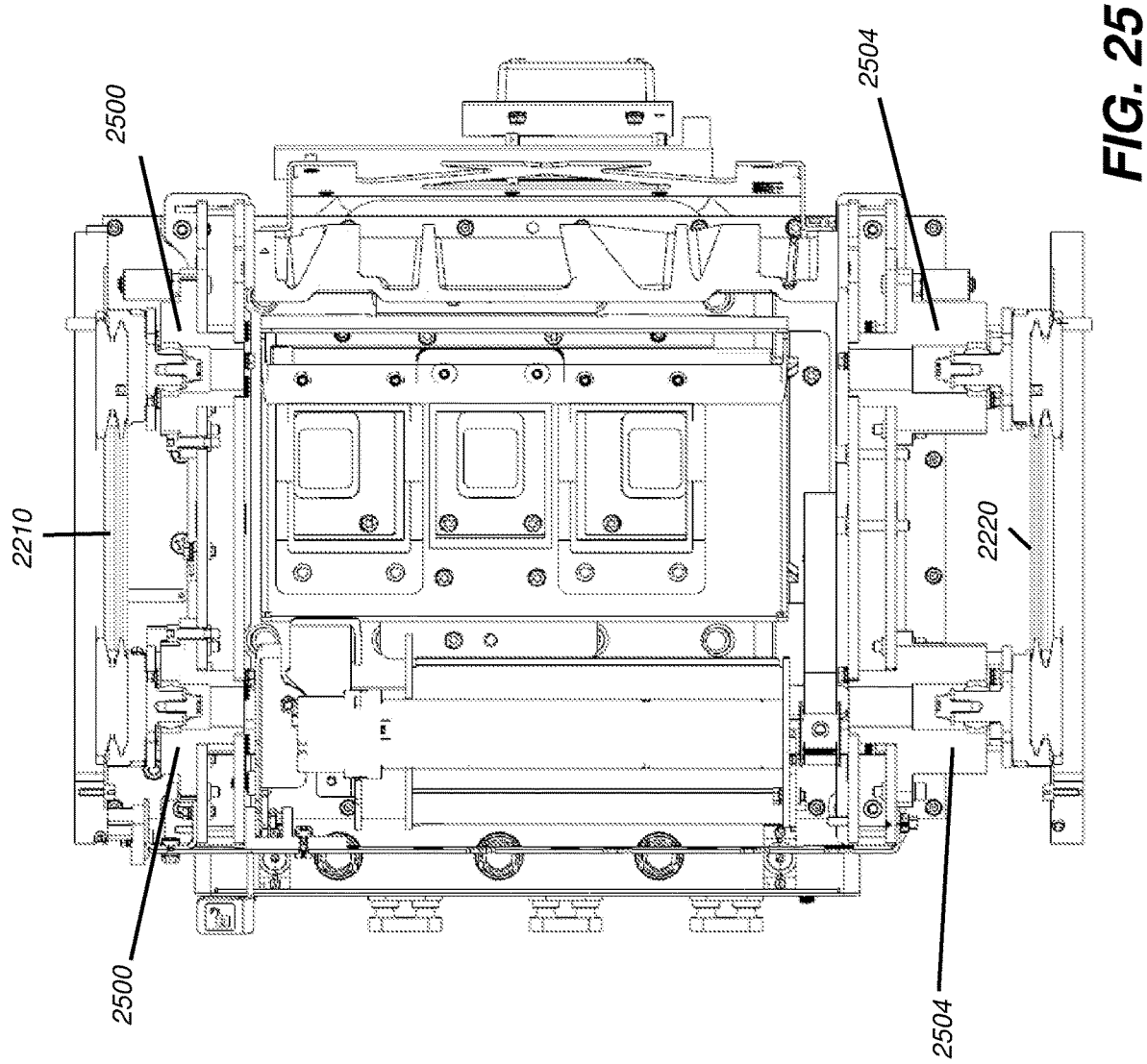
FIG. 25 is a cross-sectional view of a portion of the transport assembly, taken through four bearing mounts.

FIG. 25 is a cross-sectional view of a portion of transport assembly 170, taken through the four bearing mounts 2500 and 2504 that provide an exact constraint arrangement for the transport mechanics. Bearing mounts 2500 are provided for fitting within upper rail 2210. Bearing mounts 2504 fit within lower rail 2220.

Figure 26:
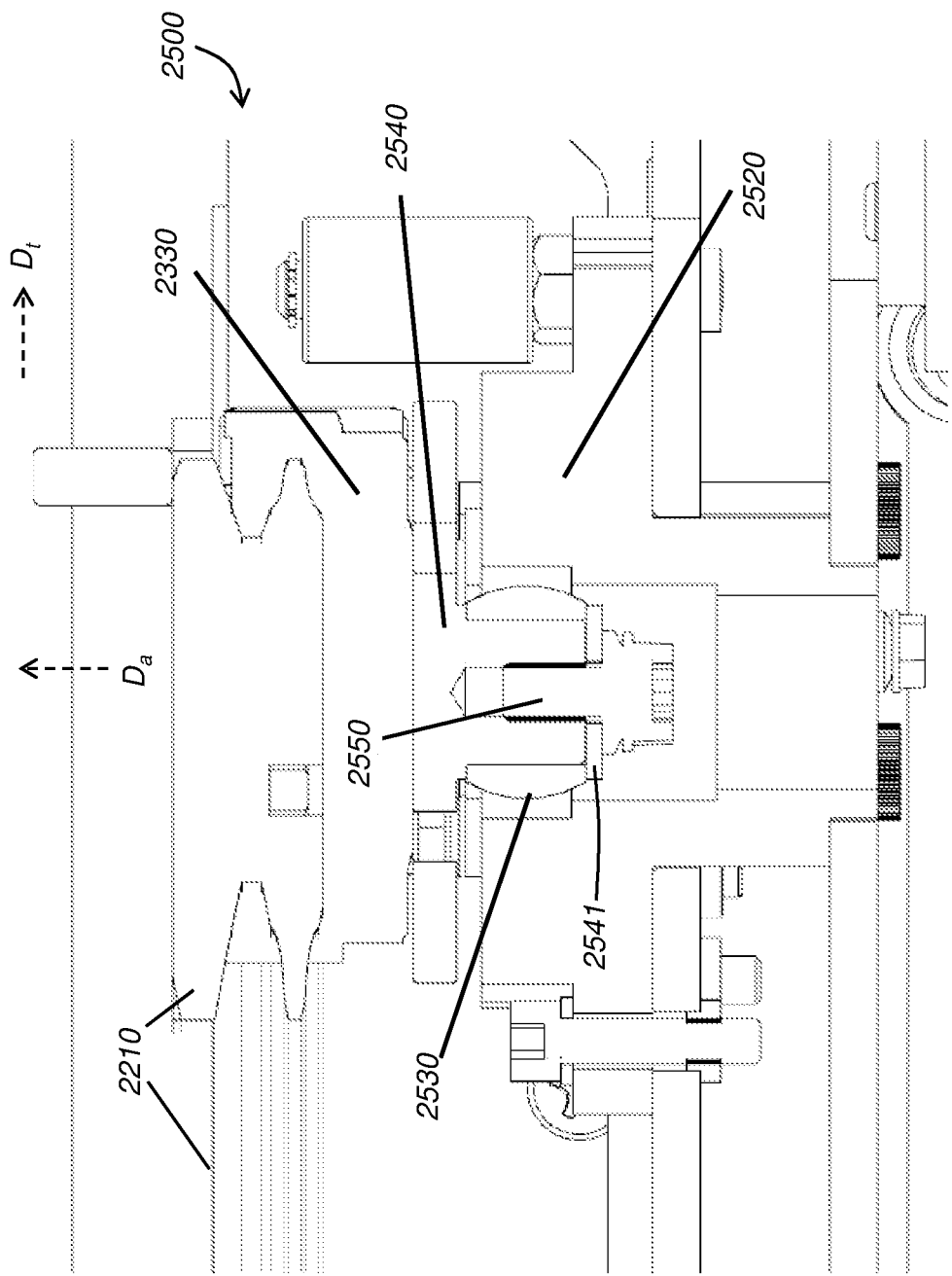
FIG. 26 is a cross-sectional drawing that shows an enlarged view of an upper bearing mount in position along the upper rail.

FIG. 26 is a cross-sectional drawing that shows an enlarged view of upper bearing mount 2500 in position along upper rail 2210. A bearing carriage 2330 (also referred to herein as a slidable mounting plate) provides a coupling to a frame mount 2520 for the x-ray source. A flanged connector 2540 is allowed a measure of gimbal rotation through spherical bearing 2530. Spherical bearing 2530 rotates about a mounting post 2550, during translation of the transport assembly 170 along transport direction $D_t$. Translation is constrained in the axial direction $D_a$ due to no spacing tolerance between flange 2541 of flanged connector 2540 and the spherical bearing 2530. There is, effectively, no axial ($D_a$) movement of the gantry allowed by bearing mount 2500.

Figure 27:
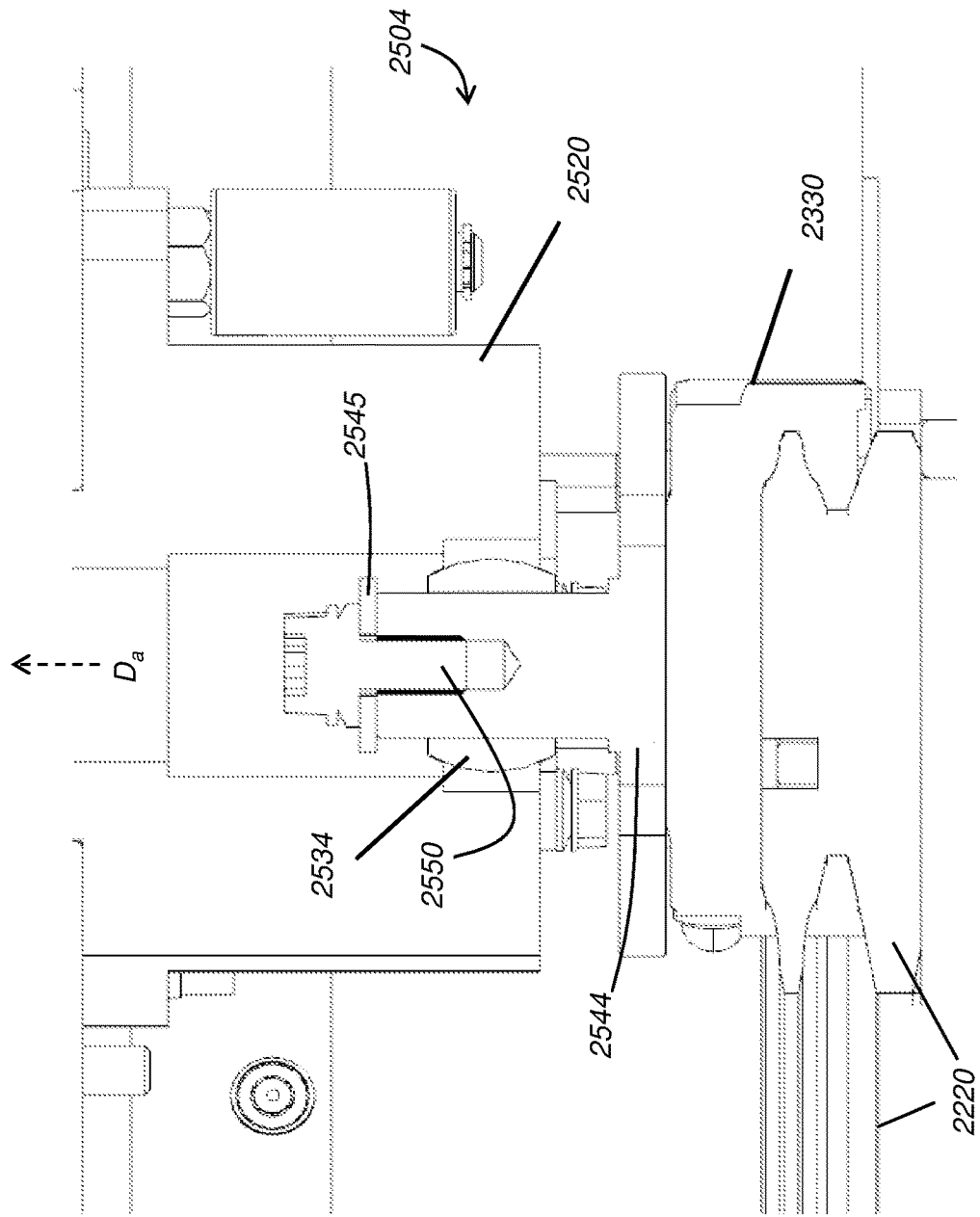
FIG. 27 is a cross-sectional drawing that shows an enlarged view of a lower bearing mount in position along the lower rail.

FIG. 27 is a cross-sectional drawing that shows an enlarged view of a lower bearing mount 2504 in position along the lower rail 2220. The weight of transport assembly 170 provides a nesting force against a spherical bearing 2534. That is, gravity can be considered to be the nesting force for exact constraint design of the transport assembly 170. Similar to the upper bearing mount of FIG. 26, spherical bearing 2534 provides a gimbaled connection between the frame mount 2520 and lower rail 2220 using the bearing carriage 2330 (or slidable mounting plate). Unlike the upper bearing mount arrangement of FIG. 26, the lower spherical bearing 2534 and flanged connector 2544 allows a measure of play in the axial direction $D_a$, due to the spacing between flange end 2545 of flanged connector 2544 and the spherical bearing 2534. This spacing may range between about 5 mm and about 20 mm, but preferably is maintained at about 10 mm or less. This added degree of freedom, although this removal of the axial constraint allows only a small amount of movement in the $D_a$ direction, helps to compensate for the effects of weight shift along the curved rails. Weight shift can cause frame deflection due to the weight shift along the curved rails. The added degree of freedom also helps to compensate for structural deflection due to the change in loading along the curved rails during scanning. This can also help to compensate for manufacturing variations.

Figure 28A:
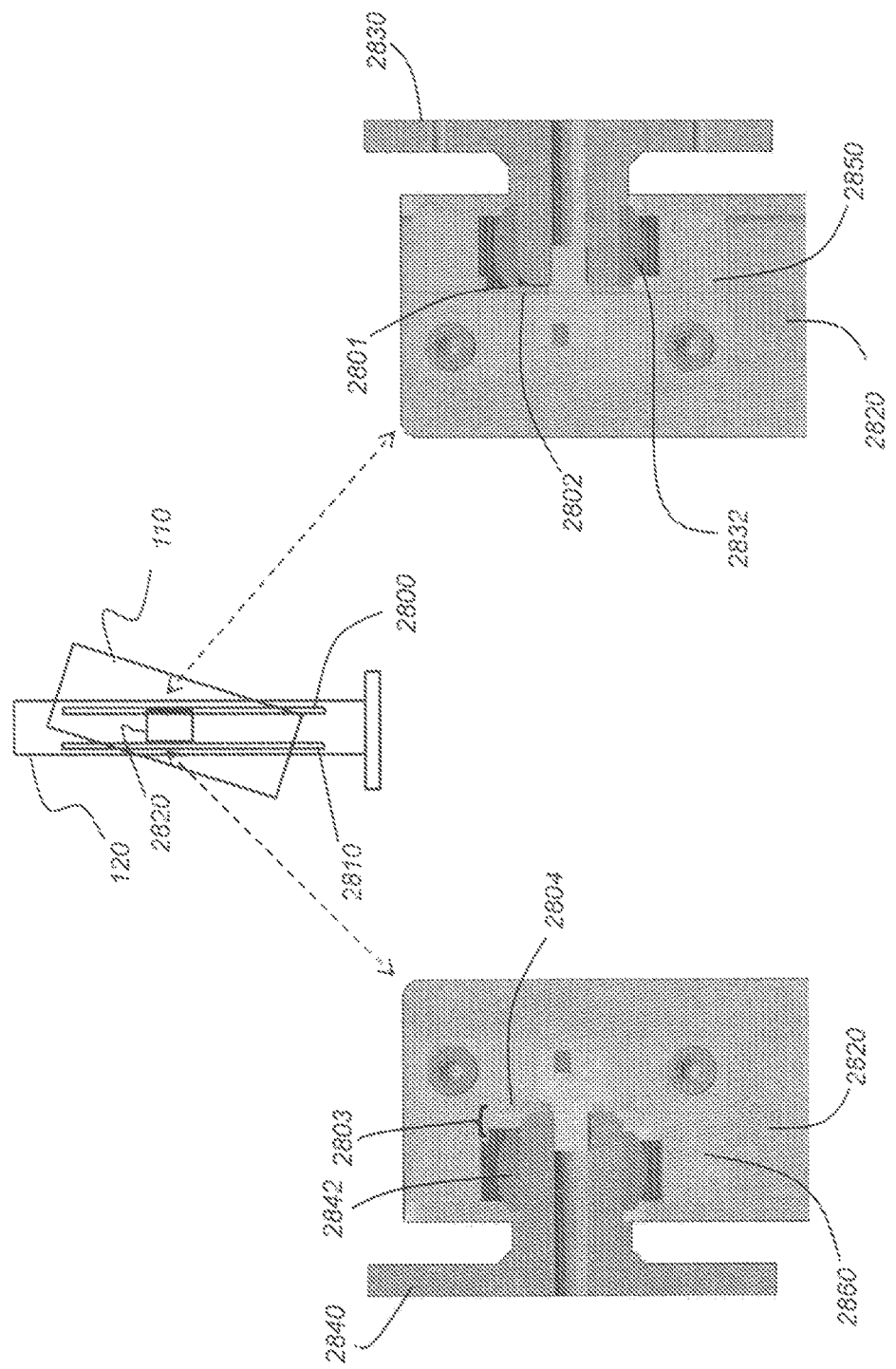
FIG. 28A shows a carriage mount for vertical transport of the scanner.
Figure 28B:
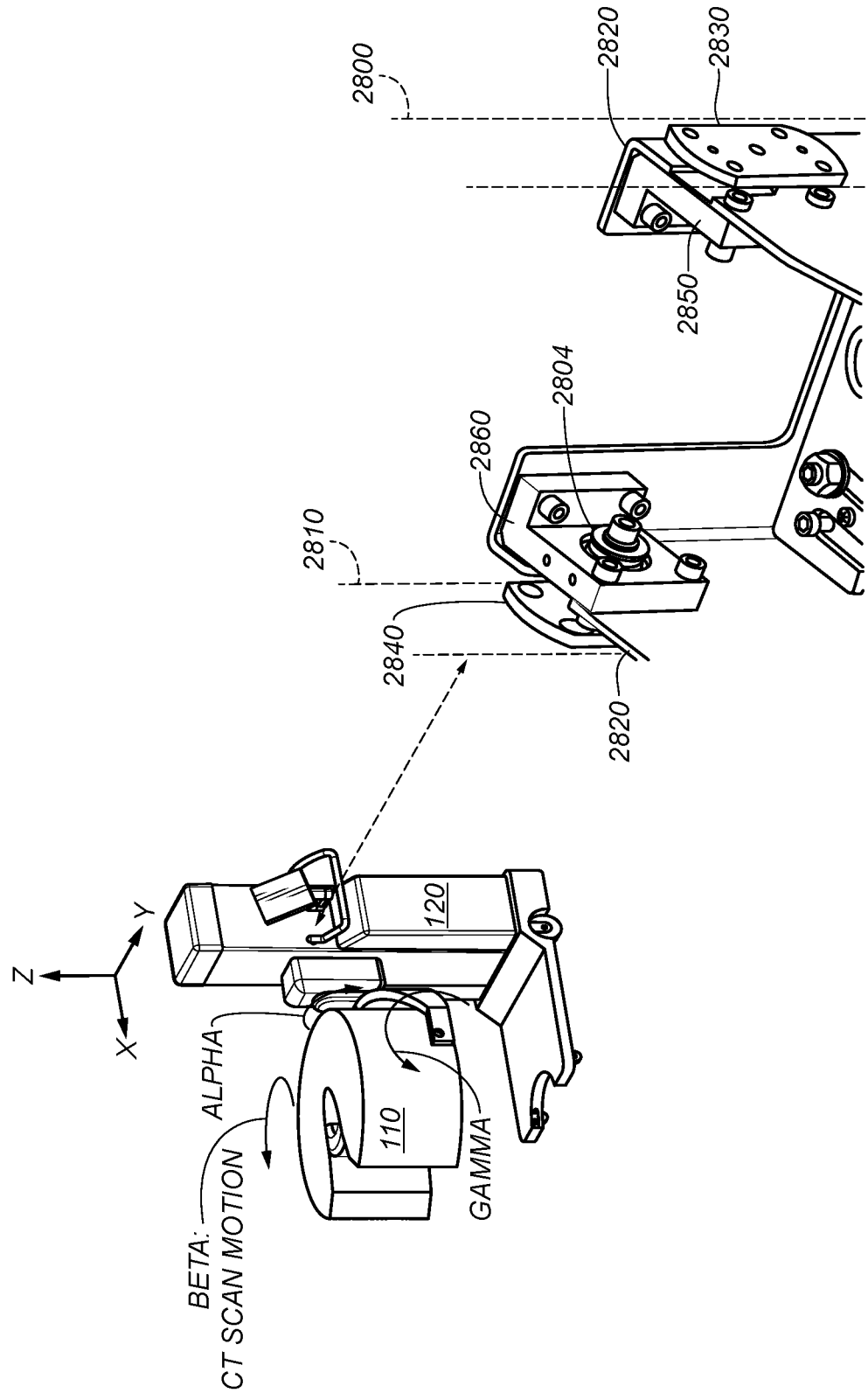
FIG. 28B shows a perspective view of the carriage mount.

The vertical carriage for movement of scanner 110 along a transport path using vertical column 120, as shown in FIG. 6A, for example, also presents a similar challenge for handling and positioning the weight of the imaging system. Referring to FIG. 28A, a carriage mount 2820 for scanner 110 travels vertically between first and second guide rails 2800 and 2810 within column 120. Guide rails 2800 and 2810 define a vertical transport path for vertical translation of scanner 110. A slide mounting plate 2830 is attached to carriage mount 2820 using attachment pivot block 2850, which may also be referred to herein as a frame mount, and has a spherical bearing 2832 that allows gimbaling for the corresponding side of carriage mount 2820 (right side in the view of FIG. 28A) but constrains translation parallel to the axis that extends horizontally between guide rails 2800 and 2810, due to the flange 2802 configured to substantially abut spherical bearing 2832 at point 2801. On the other side (left side in the view of FIG. 28A), a slide mounting plate 2840 is attached to carriage mount 2820 using attachment pivot block 2860, which may also be referred to herein as a frame mount, and similarly has a spherical bearing 2842 that allows gimbaling and, additionally, allows some translation in the direction parallel to the horizontal axis, due to the spacing tolerance 2803 between flange 2804 and spherical bearing 2842, which is spaced similarly to the spacing disclosed above. FIG. 28B shows a perspective view of the same slide mounting plates 2830, 2840, as shown in FIG. 28A, positioned on side rails 2800 and 2810.

Figure 28C:
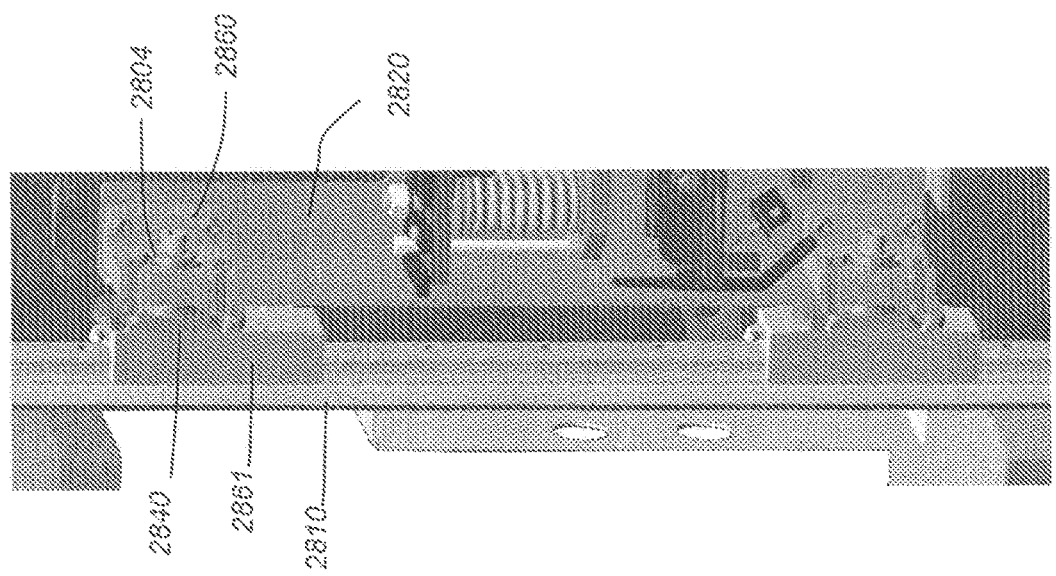
FIG. 28C shows a close-up perspective view of slide mounting plates along one side of the carriage mount.

FIG. 28C is a perspective view that shows slide mounting plates 2840 along one side of carriage mount 2820.

FIG. 28D shows a portion of a complete carriage mount assembly, as fabricated between guide rails 2800, 2810, wherein attachment pivot blocks (or frame mounts) 2850, 2860, are mounted to the guide rails 2800, 2810, using slidable mounting plates 2851 and 2861, respectively, which are slidably affixed to mating slides on the guide rails 2800, 2810.

Figure 30:
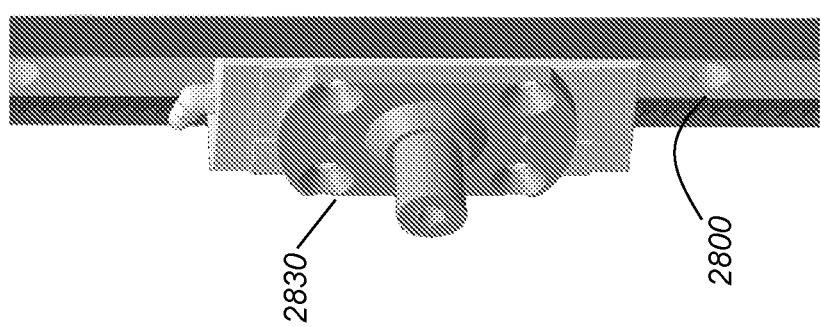
FIG. 30 shows installing a slide mounting plate into a slide on the rail.
Figure 29:
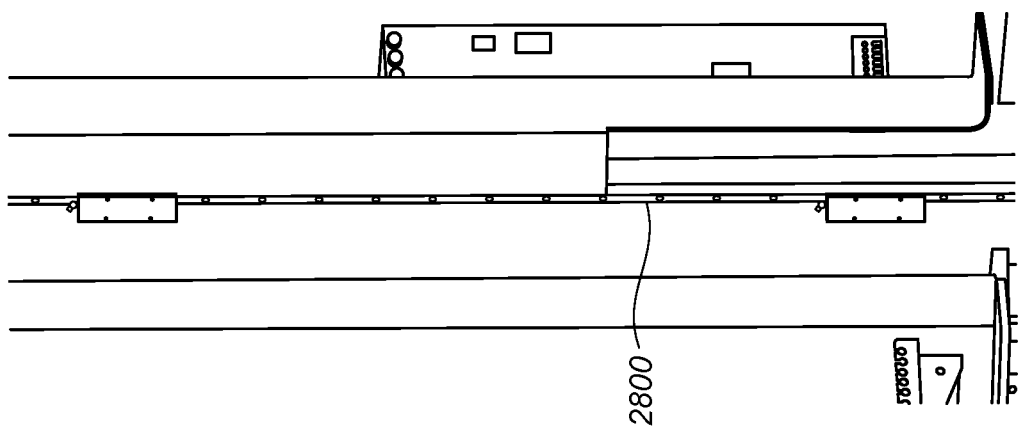
FIG. 29 shows a step of installing a side rail into the vertical column.

FIGS. 29 through 33 show various steps in the assembly process for the vertical transport apparatus. FIG. 29 shows a step of installing rail 2800 into column 120. FIG. 30 shows installing a slidable mounting plate 2851 into a slide on the rail 2800.

Figure 31:
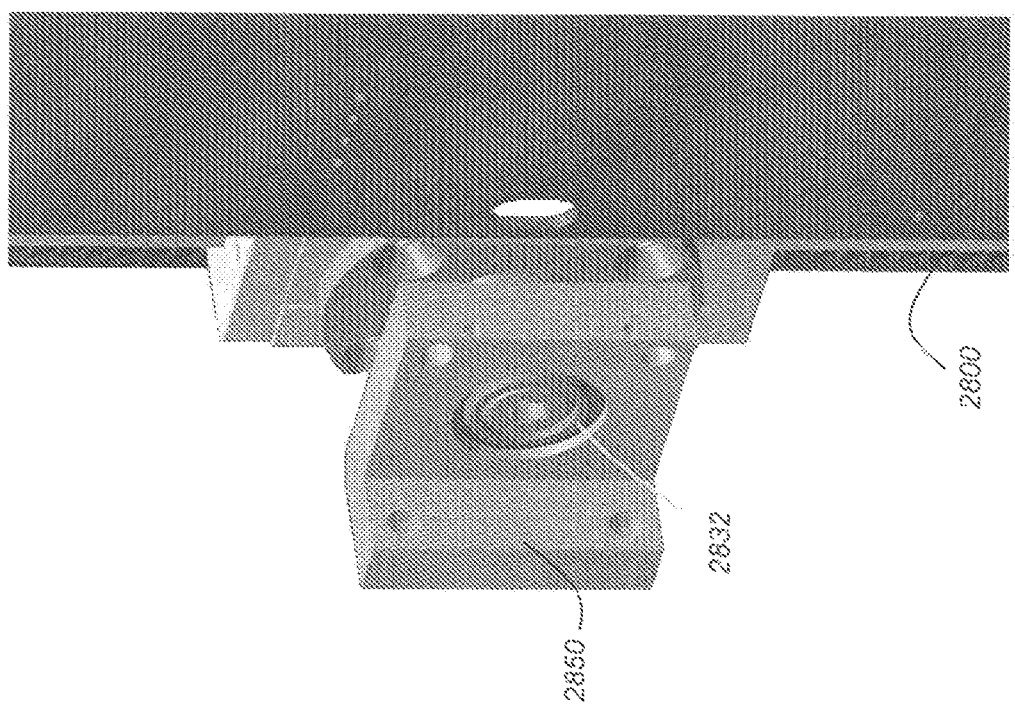
FIG. 31 shows installation of a pivoting bearing and associated pivot block.

FIG. 31 shows installation of a pivoting bearing 2832 and associated pivot block 2850.

Figure 32:
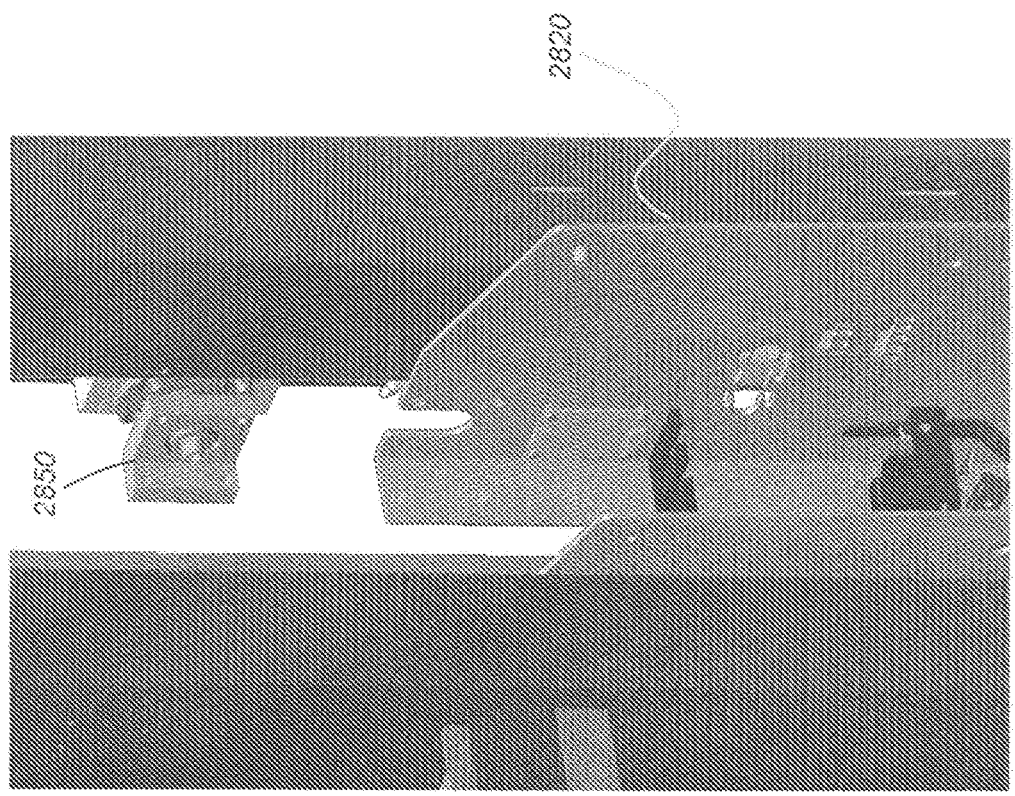
FIG. 32 shows installation of the carriage mount between corresponding pivot blocks for each rail.

FIG. 32 shows installation of carriage mount 2820 between corresponding pivot blocks for each rail, wherein pivot block 2850 is visible.

Figure 33:
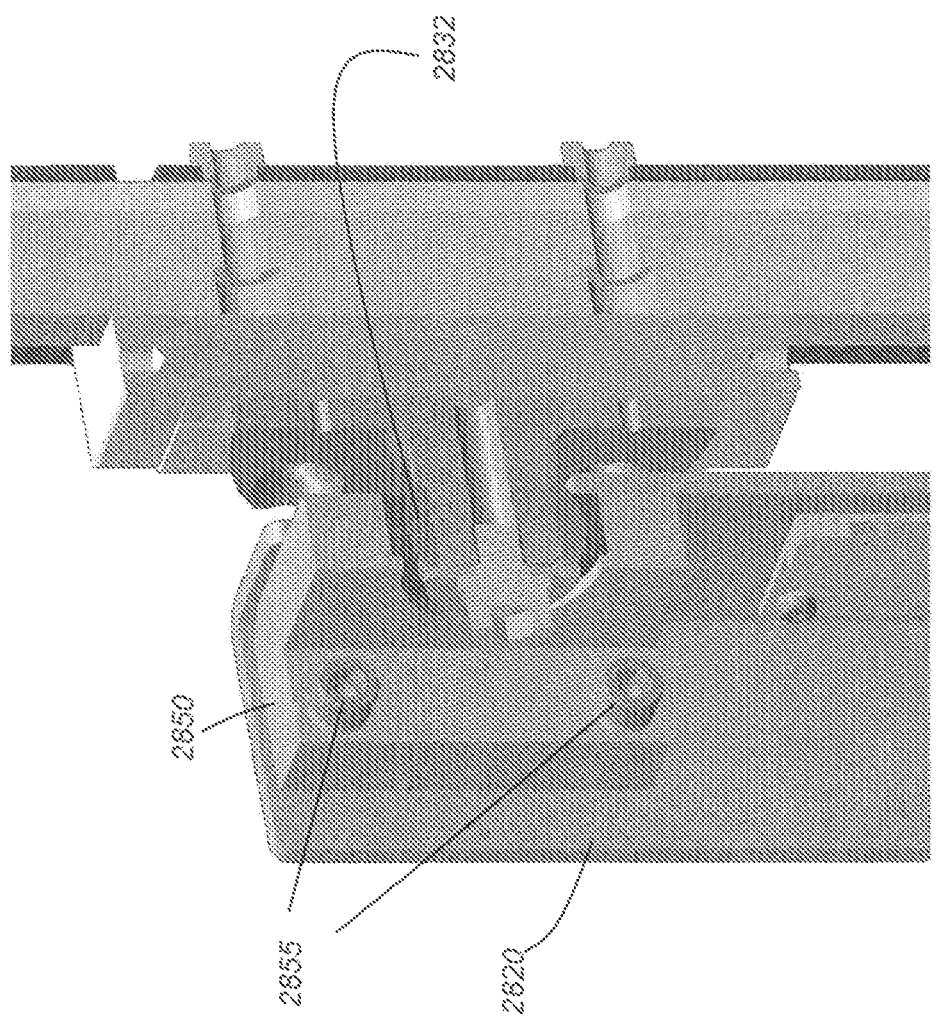
FIG. 33 shows a cross-section view of attachment of the pivot block to the carriage.

FIG. 33 shows a cross-section view of attachment of the pivot block 2850 to the carriage 2820 using screws 2855 (M6 type), according to one embodiment.

Figure 34:
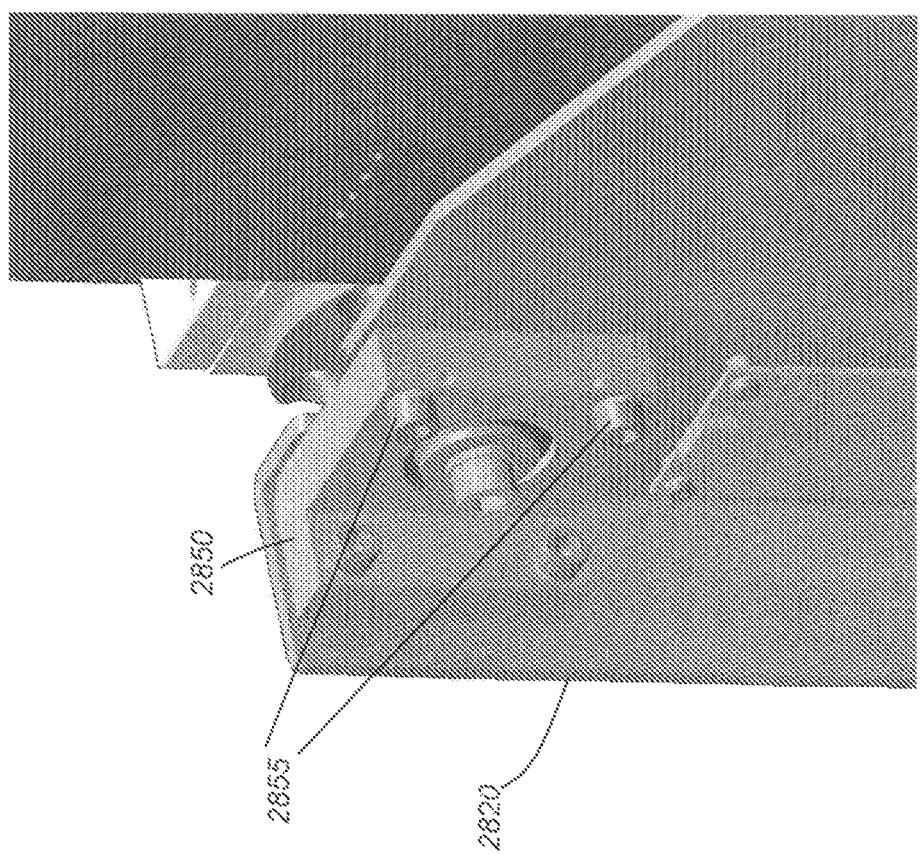
FIG. 34 shows a perspective view of attachment of the pivot block to the carriage.

FIG. 34 shows a perspective view of attachment of the pivot block to the carriage showing four screws 2855.

Consistent with at least one embodiment, exemplary methods/apparatus can use a computer program with stored instructions that perform on image data that is accessed from an electronic memory. As can be appreciated by those skilled in the image processing arts, a computer program of an embodiment herein can be utilized by a suitable, general-purpose computer system, such as a personal computer or workstation. However, many other types of computer systems can be used to execute the computer program of described exemplary embodiments, including an arrangement of networked processors, for example.

The computer program for performing methods of certain exemplary embodiments described herein may be stored in a computer readable storage medium. This medium may comprise, for example; magnetic storage media such as a magnetic disk such as a hard drive or removable device or magnetic tape; optical storage media such as an optical disc, optical tape, or machine readable optical encoding; solid state electronic storage devices such as random access memory (RAM), or read only memory (ROM); or any other physical device or medium employed to store a computer program. Computer programs for performing exemplary methods of described embodiments may also be stored on computer readable storage medium that is connected to the image processor by way of the internet or other network or communication medium. Those skilled in the art will further readily recognize that the equivalent of such a computer program product may also be constructed in hardware.

It should be noted that the term "memory", equivalent to "computer-accessible memory" in the context of the present disclosure, can refer to any type of temporary or more enduring data storage workspace used for storing and operating upon image data and accessible to a computer system, including a database, for example. The memory could be non-volatile, using, for example, a long-term storage medium such as magnetic or optical storage. Alternately, the memory could be of a more volatile nature, using an electronic circuit, such as random-access memory (RAM) that is used as a temporary buffer or workspace by a microprocessor or other control logic processor device. Display data, for example, is typically stored in a temporary storage buffer that can be directly associated with a display device and is periodically refreshed as needed in order to provide displayed data. This temporary storage buffer can also be considered to be a memory, as the term is used in the present disclosure. Memory is also used as the data workspace for executing and storing intermediate and final results of calculations and other processing. Computer-accessible memory can be volatile, non-volatile, or a hybrid combination of volatile and non-volatile types.

It will be understood that computer program products for exemplary embodiments herein may make use of various image manipulation algorithms and processes that are well known. It will be further understood that exemplary computer program product embodiments herein may embody algorithms and processes not specifically shown or described herein that are useful for implementation. Such algorithms and processes may include conventional utilities that are within the ordinary skill of the image processing arts. Additional aspects of such algorithms and systems, and hardware and/or software for producing and otherwise processing the images or co-operating with the computer program product of the application, are not specifically shown or described herein and may be selected from such algorithms, systems, hardware, components and elements known in the art.

It should be noted that while the present description and examples are primarily directed to radiographic medical imaging of a human or other subject, embodiments of apparatus and methods of the present application can also be applied to other radiographic imaging applications. This includes applications such as non-destructive testing (NDT), for which radiographic images may be obtained and provided with different processing treatments in order to accentuate different features of the imaged subject.

Although sometimes described herein with respect to CBCT digital radiography systems, embodiments of the application are not intended to be so limited. For example, other DR imaging system such as dental DR imaging systems, mobile DR imaging systems or room-based DR imaging systems can utilize method and apparatus embodiments according to the application. As described herein, an exemplary flat panel DR detector/imager is capable of both single shot (radiographic) and continuous (fluoroscopic) image acquisition. Further, a fan beam CT DR imaging system can be used.

Exemplary DR detectors can be classified into the "direct conversion type" one for directly converting the radiation to an electronic signal and the "indirect conversion type" one for converting the radiation to fluorescence to convert the fluorescence to an electronic signal. An indirect conversion type radiographic detector generally includes a scintillator for receiving the radiation to generate fluorescence with the strength in accordance with the amount of the radiation.

Exemplary embodiments according to the application can include various features described herein (individually or in combination). Priority is claimed from commonly assigned, copending U.S. provisional patent application Ser. No. 61/710,832, filed Oct. 8, 2012, entitled "Extremity Scanner and Methods For Using The Same", in the name of John Yorkston et al., the disclosure of which is incorporated by reference.

While the invention has been illustrated with respect to one or more implementations, alterations and/or modifications can be made to the illustrated examples without departing from the spirit and scope of the appended claims. In addition, while a particular feature of the invention can have been disclosed with respect to one of several implementations, such feature can be combined with one or more other features of the other implementations as can be desired and advantageous for any given or particular function. The term "at least one of" is used to mean one or more of the listed items can be selected. The term "about" indicates that the value listed can be somewhat altered, as long as the alteration does not result in nonconformance of the process or structure to the illustrated embodiment. Finally, "exemplary" indicates the description is used as an example, rather than implying that it is an ideal. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

The invention claimed is:

1. A radiographic imaging apparatus having an x-ray source and x-ray detector, the apparatus comprising:
   elongated rigid guide rails having equivalent symmetrical shapes and spaced apart substantially in parallel;
   carriages each attached to one of the guide rails, wherein the carriages are configured to move along a length of the guide rails;
   a first type spherical bearing assembly attached to a first one of the carriages which is attached to a first one of the guide rails, the first type spherical bearing assembly configured to allow a gimbaled connection thereto while allowing substantially no axial movement, the axial movement perpendicular to the first one of the guide rails;

a second type spherical bearing assembly attached to a second one of the carriages which is attached to a second one of the guide rails, the second type spherical bearing assembly configured to allow a gimbaled connection thereto while allowing a limited amount of axial movement perpendicular to the second one of the guide rails; and frame mounts each attached to one of the first type and second type spherical bearing assemblies, the frame mounts each configured to support a portion of the imaging apparatus and to facilitate movement thereof along the guide rails.

2. The apparatus of claim 1, wherein the portion of the imaging apparatus is prevented from moving substantially away from the first one of the guide rails as it moves along the guide rails by action of the first type spherical bearing assembly, and wherein the portion of the imaging apparatus is allowed to move substantially away from or toward the second one of the two guide rails as it moves along the guide rails by action of the second type spherical bearing assembly.

3. The apparatus of claim 1, wherein the first type spherical bearing assembly comprises:
a partially spherical portion having an opening therethrough; and
a flanged cylindrical extension through the opening, wherein a length of the extension is about equal to a length of the opening through the spherical portion, and wherein a flange at a distal end of the extension abuts the spherical portion to prevent the axial movement of the spherical portion.

4. The apparatus of claim 1, wherein the second type spherical bearing assembly comprises:

a partially spherical portion having an opening therethrough; and
a flanged cylindrical extension through the opening, wherein a length of the extension is greater than a length of the opening through the spherical portion, and wherein a flange at a distal end of the extension prevents the spherical portion from traveling off the end of the extension but allows limited movement of the spherical portion along the extension.

5. The apparatus of claim 1, wherein the guide rails are shaped in the form of equivalent symmetrical curves.

6. The apparatus of claim 1, wherein the guide rails are shaped in the form of equivalent symmetrical arcs.

7. The apparatus of claim 1, wherein the guide rails are shaped in the form of straight guide rails.

8. The apparatus of claim 1, wherein the limited amount of axial movement perpendicular to the second one of the guide rails about 10 mm or less.

9. The apparatus of claim 1, wherein the carriages are configured to slide along a length of the guide rails.

10. The apparatus of claim 1, wherein the frame mounts are each configured to support the source and detector and to facilitate movement thereof along the guide rails.

11. The apparatus of claim 10, wherein the frame mounts are each configured to support the source and detector and to facilitate bidirectional vertical movement thereof along vertical, linear guide rails.

12. The apparatus of claim 10, wherein the frame mounts are each configured to support the source and detector and to facilitate revolving movement thereof along arc shaped guide rails.

* * * * *